(12) United States Patent
Jung et al.

(10) Patent No.: US 7,400,754 B2
(45) Date of Patent: Jul. 15, 2008

(54) METHOD AND APPARATUS FOR CHARACTERIZATION OF CHROMOPHORE CONTENT AND DISTRIBUTION IN SKIN USING CROSS-POLARIZED DIFFUSE REFLECTANCE IMAGING

(75) Inventors: Byungjo Jung, Irvine, CA (US); Bernard Choi, Huntington Beach, CA (US); Anthony J. Durkin, Costa Mesa, CA (US); J. Stuart Nelson, Laguna Niguel, CA (US)

(73) Assignee: The Regents of the University of California, Oakland, CA (US)

( * ) Notice: Subject to any disclaimer, the term of this patent is extended or adjusted under 35 U.S.C. 154(b) by 789 days.

(21) Appl. No.: 10/818,918

(22) Filed: Apr. 7, 2004

(65) Prior Publication Data

US 2005/0030372 A1    Feb. 10, 2005

Related U.S. Application Data

(60) Provisional application No. 60/461,645, filed on Apr. 8, 2003.

(51) Int. Cl.
*H04N 7/18* (2006.01)
(52) U.S. Cl. .......................................... 382/128; 348/77
(58) Field of Classification Search ................... 382/128
See application file for complete search history.

(56) References Cited

U.S. PATENT DOCUMENTS

| | | | | |
|---|---|---|---|---|
| 5,875,264 | A | * | 2/1999 | Carlstrom .................... 382/181 |
| 5,961,457 | A | * | 10/1999 | Raylman et al. ............. 600/436 |
| 6,081,612 | A | * | 6/2000 | Gutkowicz-Krusin et al. .... 382/128 |
| 6,215,893 | B1 | * | 4/2001 | Leshem et al. ............... 382/128 |
| 6,587,539 | B2 | * | 7/2003 | Oikawa ........................ 378/19 |
| 2001/0033364 | A1 | * | 10/2001 | Cabib et al. .................. 351/221 |

* cited by examiner

*Primary Examiner*—Jingge Wu
*Assistant Examiner*—John W Lee
(74) *Attorney, Agent, or Firm*—Daniel L. Dawes; Myers Dawes Andrus & Sherman LLP

(57) ABSTRACT

A digital imaging system provides color information of an entire port wine stain or other skin condition with a single image in CIE L*a*b* color space (L*, a*) derived from RGB pixel data (R, G, B). Cross-polarization optics produce marked reduction in specularly reflected light in the images. A patient positioning device allows for repeatable positioning of the patient's head or body portion. The digital nature of the system provides a near real-time mapping of melanin and erythema or other skin chromophore metrics. The cross-polarized diffuse reflectance color digital imaging system obtains subsurface skin color information and acquisition of facial images in a reproducible fashion at a fixed distance from an illumination source at optimized angles of view depending on the region of interest being imaged.

34 Claims, 14 Drawing Sheets

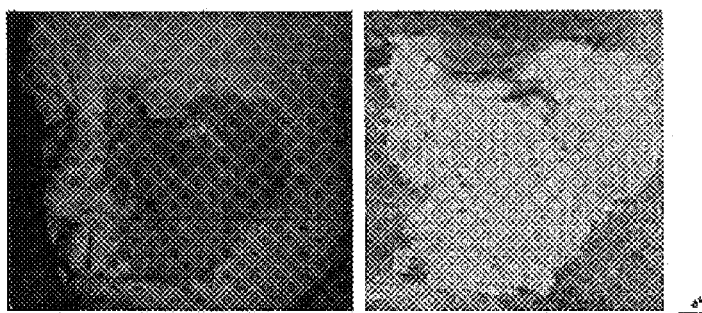
FIG. 17A
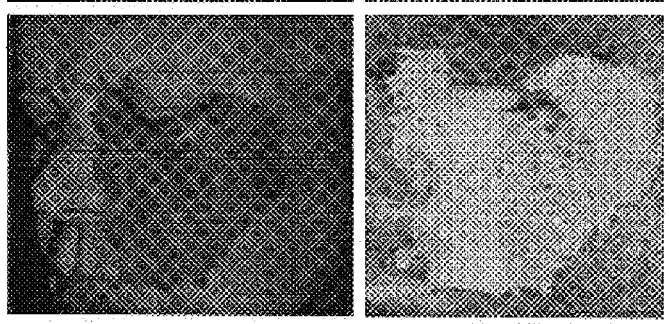
FIG. 17B
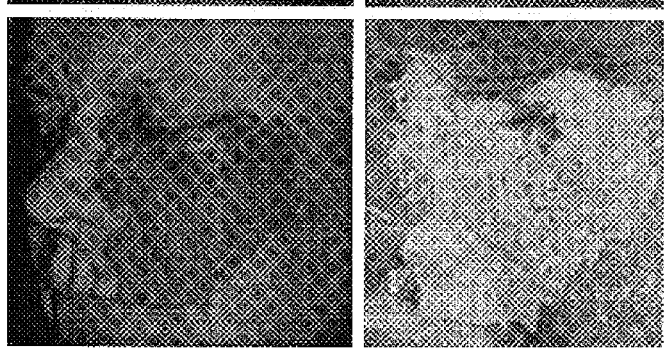
FIG. 17C

METHOD AND APPARATUS FOR CHARACTERIZATION OF CHROMOPHORE CONTENT AND DISTRIBUTION IN SKIN USING CROSS-POLARIZED DIFFUSE REFLECTANCE IMAGING

RELATED APPLICATIONS

The present application is related to U.S. Provisional Patent Application, Ser. No. 60/461,645, filed on Apr. 8, 2003, which is incorporated herein by reference and to which priority is claimed pursuant to 35 USC 119.

This invention was made with Government support under Grant Nos. AR43419 & GM62177, awarded by the National Institutes of Health. The Government has certain rights to this invention.

BACKGROUND OF THE INVENTION

1. Field of the Invention

The invention is directed to the field of optical imaging of skin and in particular to a noncontact imaging system for rapidly and quantitatively characterizing skin using a digital camera incorporating crossed-polarizers and an image analysis method.

2. Description of the Prior Art

Port wine stain (PWS) birthmark is a congenital, progressive vascular malformation of the skin that occurs in an estimated 7 children per 1,000 live births and typically occur on the face and neck. Approximately 1,500,000 individuals in the United States and thirty-two million people worldwide have PWS birthmarks. Histopathological studies of PWS show a normal epidermis overlying an abnormal plexus of dilated blood vessels located in the dermis. Epidermal thickness (50-150 μm) and melanin absorption, as well as PWS blood vessel diameter (30-300 μm) and depth distribution (150-1000 μm) vary on an individual patient basis and even between different areas on the same patient.

Since most of the malformations occur on the face, PWS is a clinically significant problem in the majority of patients. PWS should not be considered a cosmetic problem but a disease with potentially devastating psychological and physical complications. Personality development is adversely influenced in virtually all patients by the negative reaction of others to a "marked" person. Detailed studies have documented lower self-esteem in such patients and problems with interpersonal relationships. Studies have indicated a high level of psychological morbidity in PWS patients resulting from feelings of stigmatization that are frequently concealed in casual social interactions. In childhood, PWS are flat red macules. Lesions tend to darken progressively to purple, and by middle age, they often become raised as a result of the development of vascular nodules. The hypertrophy of underlying soft tissue, which occurs in approximately two-thirds of lesions, further disfigures the facial features of many patients.

Historically, therapeutic approaches to treatment PWS have included ionizing radiation, dermabrasion, cryosurgery, and electrotherapy. Clinical results using these methods were unsatisfactory due to cosmetically unacceptable scarring post treatment. Pulsed dye lasers (PDL) are currently used for the clinical management of PWS patients. PDL treatment produces reasonably good results in a limited population of PWS patients due to its ability to destroy selectively dermal blood vessels. Yellow light ($\lambda=585$ nm to 595 nm wavelength) emitted by this laser is preferentially absorbed by hemoglobin (the major chromophore in blood) in the dilated PWS blood vessels where, after being converted to heat, causes thermal damage and thrombosis. PDL treatments are currently administered by moving a laser handpiece, which creates a 5-10 mm diameter spot on the skin surface, in a methodical fashion across the entire PWS such that adjacent sites are treated sequentially.

Presently, patients are treated using laser parameter selection based on clinical judgment of the physician. A number of PWS characteristics such as size, color, anatomical location, and patient age, have been considered as prognostic parameters of response to PDL therapy. To date, none of these has been accepted as a reliable predictor of therapeutic outcome. Treatment results vary in large part due to site-to-site and interpatient variability in epidermal melanin absorption, PWS depth and blood vessel size. To further complicate the picture, absorption of laser energy by epidermal melanin reduces the light dosage reaching the blood vessels, thereby decreasing the amount of heat produced in the targeted PWS.

Because PWS blanching is almost never achieved after just one treatment, additional sessions are typically required, with a three-month interval between successive patient visits. Unfortunately, if the ultimate standard required is complete blanching of the lesion, even after many repeat treatments, complete blanching is rarely achieved where an average success rate of below 10% is experienced. We believe that this occurs primarily because the attending physician is unable to select the optimal treatment parameters for a specific PWS lesion.

Pretreatment knowledge of tissue parameters on an individual patient basis can result in optimization of PWS laser therapy. However, due to a dearth of clinically accepted devices for determining these parameters, clinicians must still rely on subjective qualities such as PWS skin appearance and personal experience to determine treatment parameters (e.g., wavelength, pulse duration, spot size, light dose, and cryogen spray cooling factors) to use on each patient.

Commercial devices, such as reflectance spectrophotometers and tristimulus colorimeters, can provide quantitative information on skin erythema and melanin. In the biomedical field, these devices have been used to quantify skin color changes induced by UV radiation exposure. Erythema indices have been measured that were compared with subjective evaluation of PWS blanching provided by clinicians. Decreases in erythema indices correlated well with improved PWS blanching, demonstrating the feasibility of using these erythema metrics in management of PWS patients undergoing therapy. As the PWS is blanched, the value of the erythema metric used would approach that of the surrounding normal skin. Furthermore, if the erythema metric changes minimally between two successive visits, the clinician could alter treatment parameters or deem the patient as a nonresponder and stop treatment. This is especially important for treatment of children, as they routinely are subjected to full anesthesia prior to each treatment session; it is especially important to identify children who are unresponsive to laser therapy to avoid unnecessary anesthesia.

The basic operation of common commercial devices involves irradiation of skin with a light source and capture of reflected light using a combination of limited bandwidth photodetectors. The Dermaspectrophotometer™, reflectance spectrophotometer (Gyberderm inc. Media, Pa.) emits light at green and red wavelengths for semi-quantitative calculation of erythema and melanin indices, respectively. A single small-area photodetector detects reflected light at each emission wavelength, and erythema and melanin indices are computed. Similarly, tristimulus calorimeters illuminate the skin with white light and reflected light is detected with three filtered photodiodes sensitive to either red, green, or blue (RGB) light.

With these kinds of reflectance spectrophotometers, melanin and erythema indices are determined using one of several proposed algorithms. These algorithms typically involve algebraic expressions incorporating reflectance values measured at three or four select wavelengths. The data is subsequently converted to the Commission Internationale de l'Eclairage (CIE) L*a*b* color space (Table 1), which consists of three quantities: L* describes the reflected light intensity and varies between 0 (e.g., black) and 100 (e.g., white); a* describes color saturation and varies between −60 for green and +60 for red; and b* also describes color saturation and varies between −60 for blue and +60 for yellow. Studies have shown that L* and a* are viable indicators of melanin and erythema, respectively. Other studies have shown that b* and combinations of L* and b* are viable indicators of melanin.

TABLE 1

Color range of parameters in CIE L*a*b* color space

| CIE Parameters | Quantitative Range |
| --- | --- |
| L* (Light Intensity) | 0 (Black) to +100 (White) |
| a* (Saturation) | −60 (Green) to +60 (Red) |
| b* (Saturation) | −60 (Blue) to +60 (Yellow) |

The L*a*b* coordinate axes are orthogonal to one another (FIG. 1). Studies have shown that a* and L* values (Table 2) represent the degree of skin erythema or hemoglobin content and the degree of skin pigmentation or melanin content, respectively.

TABLE 2

Definitions of L*, a*, and Δa*

| Parameters | Definition |
| --- | --- |
| L* | Indicator of melanin content<br>Higher value represents lower melanin content |
| a* | Indicator of erythema, which is directly related to hemoglobin content<br>Higher value represents higher erythema |
| Δa* | Indicator of erythema difference between PWS and normal skin<br>Positive values indicate that the region of interest has more erythema than the reference normal skin regions |

Although reflectance measurement techniques can provide valuable information on PWS skin, they are generally limited in usefulness by practical considerations. They provide information on only a small area (~10-15 mm in diameter) per measurement; thus, it may be time consuming to measure an entire PWS. For example, for a PWS of 100 cm$^2$ area, characterization of the entire area would require over 100 measurements. Furthermore, since these devices are required to be in contact with skin, variations in contact pressure can induce artifacts in the measured reflectance values. Application of excessive pressure can result in transient blanching of the PWS due to blood vessel collapse, resulting in potentially large error in measured values.

A potential alternative approach that may ameliorate many of these difficulties is based on digital photography. This technology offers advantages such as computer interface for near real-time feedback, flexibility of measurement area selection, and noncontact technique. However, for a digital imaging system to provide meaningful results, parameters such as camera sensitivity, shutter speed, aperture size, magnification, and patient positioning must be controlled. Furthermore, image quality may be affected by shadowing, glare, nonuniform illumination, changes in spectral qualities of the illumination source with time and artifacts resulting from environmental lighting.

Medical imaging is critical for quality health care, yet remains unavailable to many patients in small hospitals, rural communities and underdeveloped nations. With recent developments that provide inexpensive portable computation and consumer camera systems capable of high fidelity, megapixel resolution imaging, it might be possible to somehow develop inexpensive, innovative, high-resolution imaging devices with emphasis on early detection and efficient treatment of disease and injury. What is needed is a low-cost, quantitative digital imaging system that can be applied in a quantitative way to assess in-vivo tissue. While we have chosen to focus on port wine stain (PWS) because of its high inherent optical contrast in the visible portion of the electromagnetic spectrum, the method of the invention will be applicable to a variety of tissues for which information related to changes in tissue composition is desired and not just PWS.

BRIEF SUMMARY OF THE INVENTION

The invention is a noncontact, low-cost imaging system which rapidly and quantitatively characterizes skin. A digital camera is modified to incorporate crossed-polarizers, and combined with a novel image analysis method. The unique analysis technique provides quantitative color information with a Commission Internationale de l'Éclairage (CIE) L*a*b* image that can be used to deduce spatially resolved melanin and erythema indices. Color images and processed CIE color space images will enable pixel-by-pixel tissue analysis.

The apparatus and methodology of the invention is amenable for use by clinicians for quantitative evaluation of vascular and pigmentation diseases on an individual patient basis, including but not limited to PWS laser therapy, and for quantification of chromophore content for in vitro skin phantoms and in vivo skin. The illustrated embodiment is directed to the context of port wine stain (PWS), however any dermal application is considered within the scope of the invention.

The invention is more generally an imaging system with the ability to quantify chromophore content in skin. The system of the invention can accommodate multiple optical filters to provide an inexpensive spectral imaging solution. Inverse models are used to solve the problem of recovering chromophore content from reflectance spectral images.

The digital imaging system of the invention provides color information of an entire port wine stain or other skin chromophore content with a single image. Polarization optics produce marked reduction in specularly reflected light in the images. A patient positioning device allows for repeatable positioning of the patient's head or body portion. The digital nature of the system provides a near real-time mapping of melanin and erythema or other skin chromophore metrics. The cross-polarized diffuse reflectance color imaging system obtains subsurface skin color information and acquisition of facial images in a reproducible fashion at a fixed distance from an illumination source.

The invention in another embodiment is an image analysis method to characterize quantitatively erythema and melanin content of hypervascular port wine stain birthmarks in human skin using a* and L* values from the Commission Internationale de l'Èclairage (CIE) L*a*b* color space.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The invention can be better visualized by turning now to the following drawings wherein like elements are referenced by like numerals.

BRIEF DESCRIPTION OF THE DRAWINGS

FIGS. 17a, 17b and 17c are photographs of the PWS patient of FIGS. 15a and 16a taken with cross-polarized diffuse reflectance color as shown in the left column and a* images of the PWS patient taken at the optimal view angle of 45° as shown in the right column. The images were acquired at three successive visits over an eight week period. The images in FIGS. 17a, 17b and 17c indicate the first, second, and third visits, respectively. The image acquisition based on the optimal view angle provides comparable qualitative skin color images and also allows to use absolute a* image for quantitative assessment in laser treatment effect of PWS.

Figure 1:
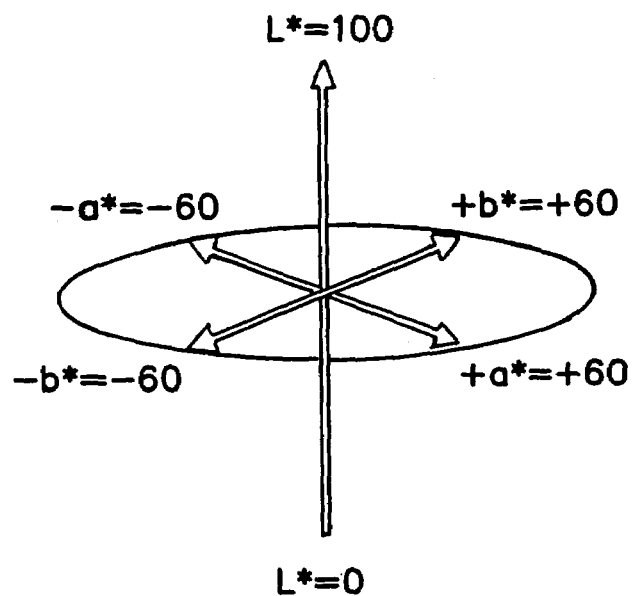
FIG. 1 is a diagram illustrating the prior art CIE L*a*b* color space.

The invention and its various embodiments can now be better understood by turning to the following detailed description of the preferred embodiments which are presented as illustrated examples of the invention defined in the claims. It is expressly understood that the invention as defined by the claims may be broader than the illustrated embodiments described below.

DETAILED DESCRIPTION OF THE PREFERRED EMBODIMENTS

Numerous factors affect the quality of information contained in each digital image. As an optical system is used to capture data from patients over a period of months to years, it is critical to characterize the sources of variation in the system and determine the sensitivity of the data to expected changes that may occur in the system components over time. The effects of curved surfaces on recovered indices, quality of crossed-polarizer extinction, drift in "color temperature" of the illumination device, errors in white balance, errors in repositioning target tissue and effects of small angular displacements in illumination and collection will impact the data analysis. We have quantified the variance associated with each of these factors and subsequently take steps to control or minimize the impact of those factors. Statistical error propagation analysis is used to determine the overall magnitude of multiple sources of error on CIE L*a*b* values computed from each raw image.

There have been numerous reports in the literature that detail investigations of skin melanin and erythema characteristics using approaches that require contact with the sample, such as reflectance spectroscopy and tristimulus colorimetry.

A popular commercial tristimulus calorimeter comparable to that commonly described in the literature is used to compare erythema and melanin metrics to those obtained with the crossed-polarizer digital imaging system of the invention. Comparison measurements are performed on both tissue phantoms and in-vivo tissue.

Image data from patients with PWS who are scheduled to undergo laser therapy is taken before treatment, after treatment and during healing phases, and compared with subjective, real-time evaluation of the patients and with subjective evaluation of unpolarized, unprocessed digital images.

The various proposed melanin and erythema metrics are optimized for skin characterization in terms of contrast, information content and orthogonality. Clinical data is reprocessed using different variations of algorithms.

The system 10 of the invention is used to provide the clinician with objective feedback on PWS treatment progress with successive patient visits. The invention is proven to be a reliable quantitative imaging system, which can be optimized for use in a variety of other compelling applications for which information related to changes in tissue composition is desired. Examples of such other applications include, but are not limited to: assessment of treatment of vitiligo and other pigmentary disorders, evaluation of treatment endpoints for psoriasis, evaluation of treatment endpoints of pigmented lesions, and assessment of subsurface changes in vasculature and pigmentation related to skin cancer.

Figure 2:
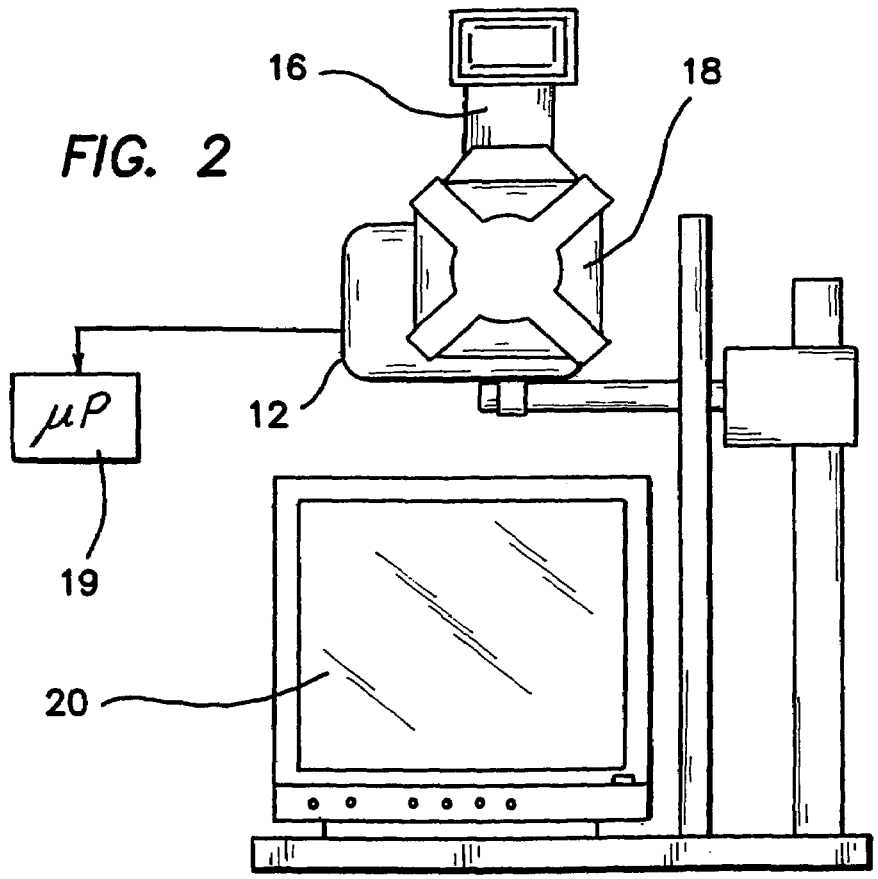
FIG. 2 is a diagrammatic front elevational view of the apparatus of the invention.

The illustrated embodiment is a digital imaging system 10 as diagrammatically depicted in FIG. 2 that can provide color information of an entire PWS with a single image. The system 10 utilizes a commercial digital camera 12 (Model DiMAGE7, Minolta Co., Osaka, Japan). Modifications have been made to the camera to incorporate uniform illumination and to implement polarization optics. A polarization analyzer or polarizer 14 is added to the lens. A flash controller 16 and macro ring 18 flash is used to obtain uniform illumination on the skin surface. Color analysis software has been written to provide images of melanin and erythema metrics. Images of PWS patients are acquired from camera 12 by computer 19 and analyzed with the software stored in computer 19. The digital output from camera 12 is displayed on monitor 20. A crossed-polarizer illumination/detection configuration can provide high discrimination between the specularly reflected light from a surface and diffuse, multiply scattered subsurface light, conferring to an imaging system a certain degree of "optical sectioning". The camera 12 is designed to allow for variation of different settings to achieve the best possible white balance for a given set of lighting conditions.

Uniform illumination is helpful for maximizing the effective dynamic range of each pixel in an image. Camera 12 provides 24-bit color information; 8 bits each of red, green, and blue. Thus, each color channel has 256 distinct values, ranging from 0 to 255. An ideal image of a 99% diffuse reflectance standard would be comprised of pixel values in each color channel of ~255. Under unsaturated lighting conditions, this can be achieved only with uniform illumination. With nonuniform illumination, pixel values in an image of a 99% standard would be less than 255, resulting in a loss of effective dynamic range.

Standard digital cameras have a built-in flash, which typically result in nonuniform illumination of the target. To reduce the severity of this problem, camera 12 is equipped with an external macro ring flash 18 (Model 1200, Minolta Co.), which is designed to increase uniformity of illumination. A second image of the same standard was taken using the macro ring flash 18, resulting in RGB pixel values of 251.7, 253.7 and 252.1, respectively, with standard deviations of ~1.

Figure 3A:
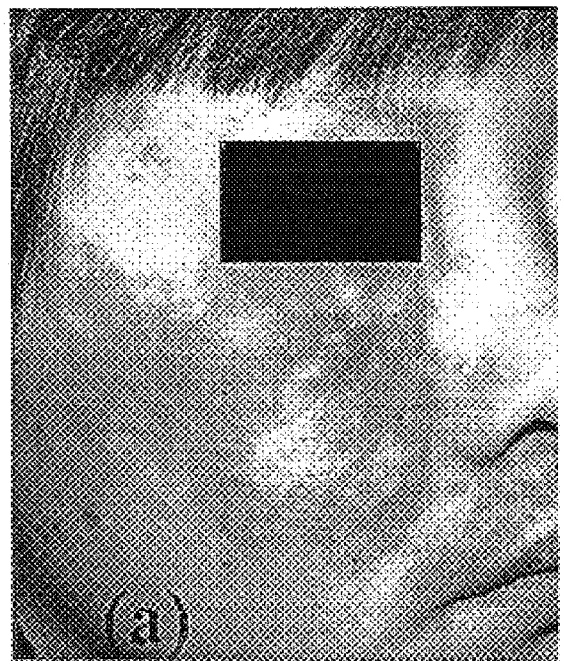
FIGS. 3a and 3b are photographic images of PWS skin taken in FIG. 3a without and in FIG. 3b with crossed polarizers. Bright spots due to specular reflectance are evident in FIG. 3a and absent in FIG. 3b.
Figure 3B:
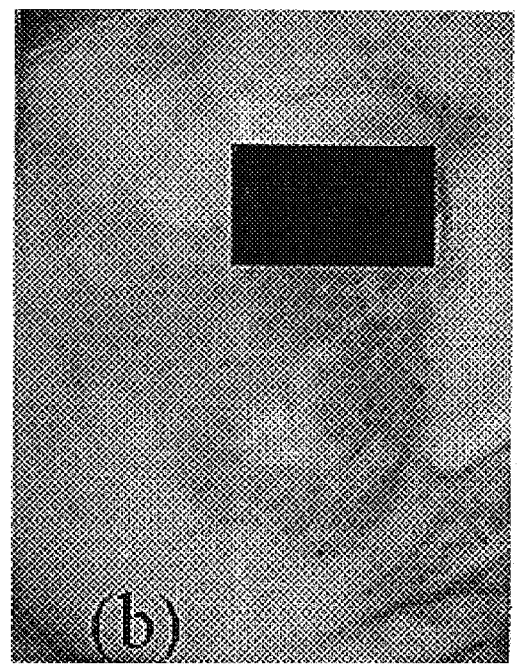

An advantage of system 10 is the use of polarization optics to remove specularly reflected light or "glare". When light is incident on skin, about 5% is reflected due to the refractive index mismatch between human skin and air. Such specularly reflected light provides information on the superficial texture of the skin surface. However, specular reflectance reduces the ability to observe subsurface structures. To illustrate this, an image of PWS skin taken without crossed polarizers is shown in FIG. 3(a). To reduce the glare caused by specular reflectance from the skin surface, a first linear polarizer 18 (Model A45-669, Edmund Industrial Optics, Barrington, N.J.) was placed in front of the macro ring flash 18; a second identical linear polarizer, denoted as analyzer 14, was placed in front of the camera lens. The polarizers were positioned such that their respective polarization axes were orthogonal. The resulting image is shown as FIG. 3(b).

Figure 4:
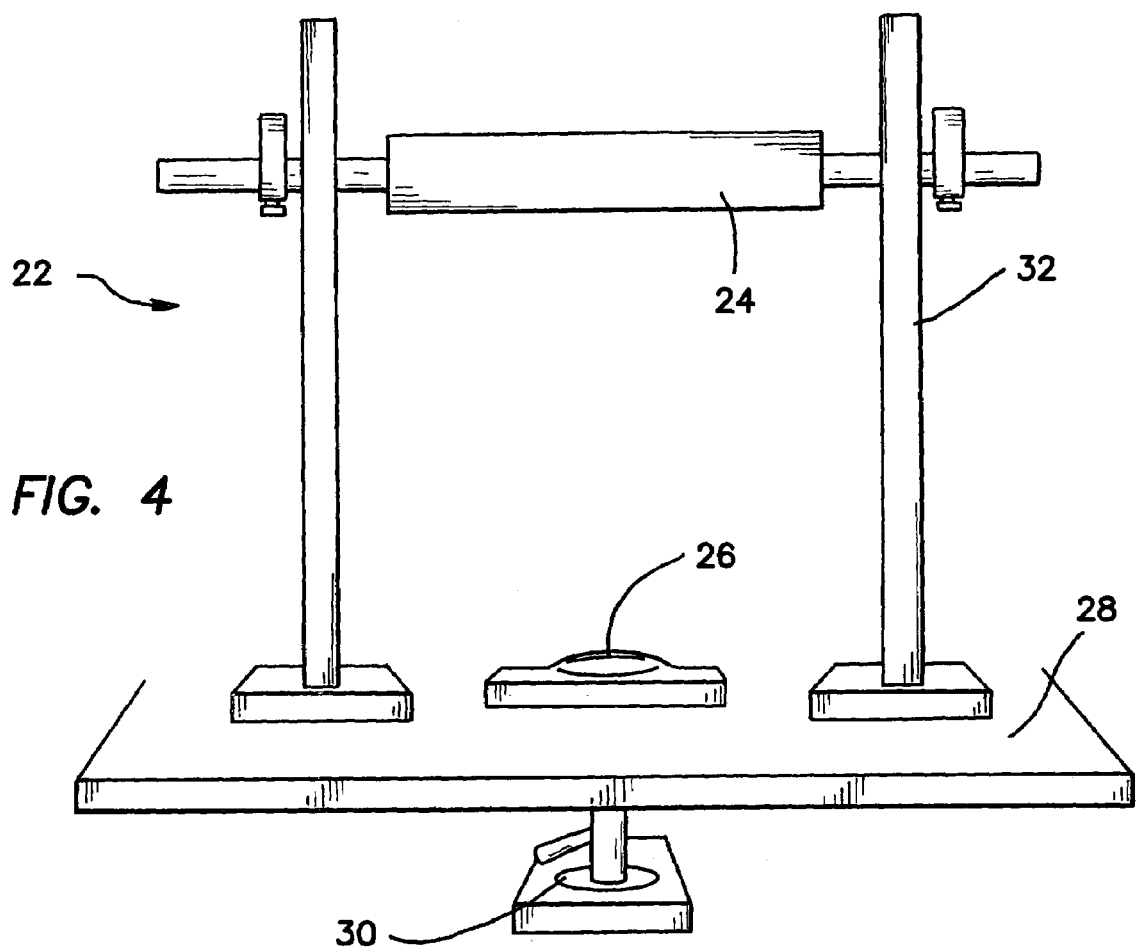
FIG. 4 is a diagrammatic front view depiction of head and chin rest used to position each patient's head in a reproducible manner.

To eliminate artifacts induced by environmental lighting, the digital images were acquired in the dark. Camera settings (shutter speed: 1/60 s, aperture size: F/8) were constant for all acquired images. To ensure that test sites identified on the skin were positioned in a reproducible manner, a patient positioning device 22 was created as depicted in the diagram of FIG. 4 comprising a head rest 24 held by frame 32 mounted on stage 28 and a chin rest 26 mounted on a rotary stage 28 adjustable by positioning lever 30 that allows for patient head positioning at angles between 0° (front view) and 90° (side view).

For purposes of comparison image processing was performed with a prior art algorithm previously described in studies employing non-imaging tristimulus calorimeters. See Malacara, D., *Color Vision and Colorimetry: Theory and Applications*, 2002, Bellingham, Wash.: SPIE. In this conventional process, erythema and melanin indices are determined by converting data from the RGB color space of each image to the CIE L*a*b* color space. RGB values for each camera pixel are first converted into device-independent CIE XYZ tristimulus values with a conversion matrix (Equation 1, below) so as to transform images as if they were acquired under average daylight illumination at a standardized blackbody temperature of 6500K:

$$\begin{bmatrix} X \\ Y \\ Z \end{bmatrix} = \begin{bmatrix} 0.412453 & 0.357580 & 0.180423 \\ 0.212627 & 0.715160 & 0.072169 \\ 0.019334 & 0.119193 & 0.950227 \end{bmatrix} \begin{bmatrix} R \\ G \\ B \end{bmatrix} \quad (1)$$

To arrive at a set of XYZ values, two RGB images are required: (1) a raw RGB image of the patient's skin and (2) an image of a 99% diffuse reflectance standards. From these images, two XYZ tristimulus images can be computed, one for skin (X, Y, Z) and the other for the calibration reference ($X_n, Y_n, Z_n$). The final step is to convert the skin XYZ images into CIE L*a*b* color images using equations 2a-2f:

$$L^* = 116 \left( \frac{Y}{Y_n} \right)^{1/3} - 16 \quad \text{for } Y/Y_n > 0.008856 \quad (2a)$$

$$L^* = 903.3 \left( \frac{Y}{Y_n} \right) \quad \text{otherwise} \quad (2b)$$

$$a^* = 500 \left[ f\left( \frac{X}{X_n} \right) - f\left( \frac{Y}{Y_n} \right) \right] \quad (2c)$$

-continued $$b^* = 200\left[f\left(\frac{Y}{Y_n}\right) - f\left(\frac{Z}{Z_n}\right)\right] \quad (2d)$$

where $$f(t) = t^{1/3} \quad \text{for } t > 0.008856 \quad (2e)$$

$$f(t) = 7.787t + 0.138 \quad \text{otherwise} \quad (2f)$$

As described above in Tables 1 and 2, L* and a* provide information on melanin and erythema content, respectively. L* describes the reflected light intensity and varies between 0 (e.g., black) and 100 (e.g., white). A larger value of L* is indicative of smaller melanin content. a* describes color saturation and varies between −60 for green and +60 for red. A larger value of a* represents higher erythema.

Figures 5A, 5B, 5C:
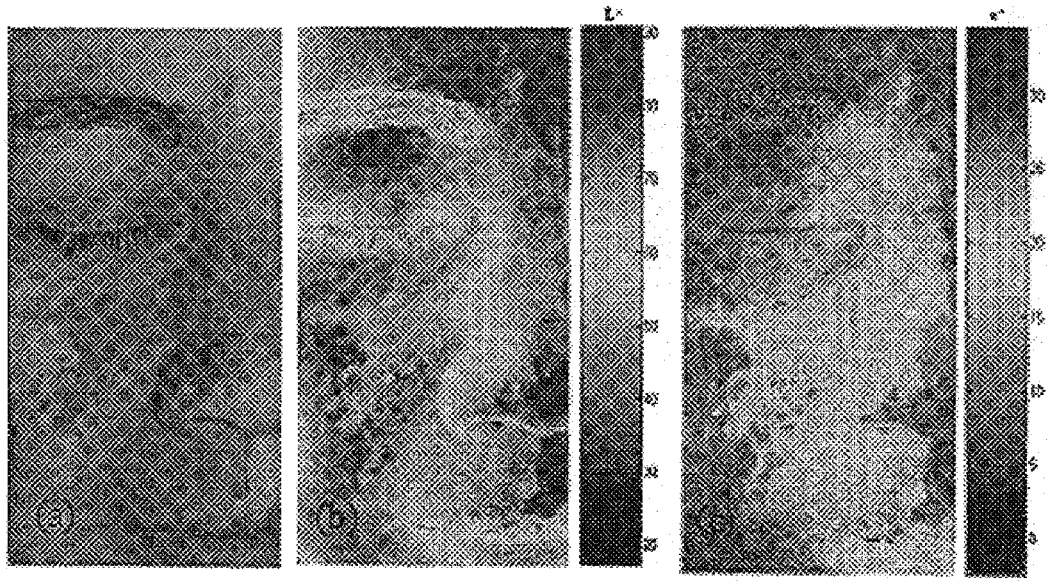
FIG. 5a is a photograph of a digital cross-polarized image of a PWS patient.
FIG. 5b is the same image as an L* image.
FIG. 5c is the same image as an a* image.

Using Equation 2, a RGB image of PWS skin as shown in the photograph of FIG. 5a is converted to the CIE L*a*b* color space as shown in the images of FIGS. 5b and 5c. In the L* image of FIG. 5b, L* values in general were in the range of 60 to 90. Regions of low L* values (e.g., L*<50) were evident in the eyebrow, eyelashes, and lip. A small region of low L* values is present also on the edge of the nose. In the corresponding region in the RGB image of FIG. 5a, a slight shadow is evident due to the curved nature of the nose edge. In the a* image of FIG. 5c, a distribution of a* values (~10 to 25) are apparent in the PWS region of the image. This type of distribution is not readily evident in the RGB image of FIG. 5a, demonstrating the better contrast of the a* image as compared to the RGB image.

Figures 6A, 6B:
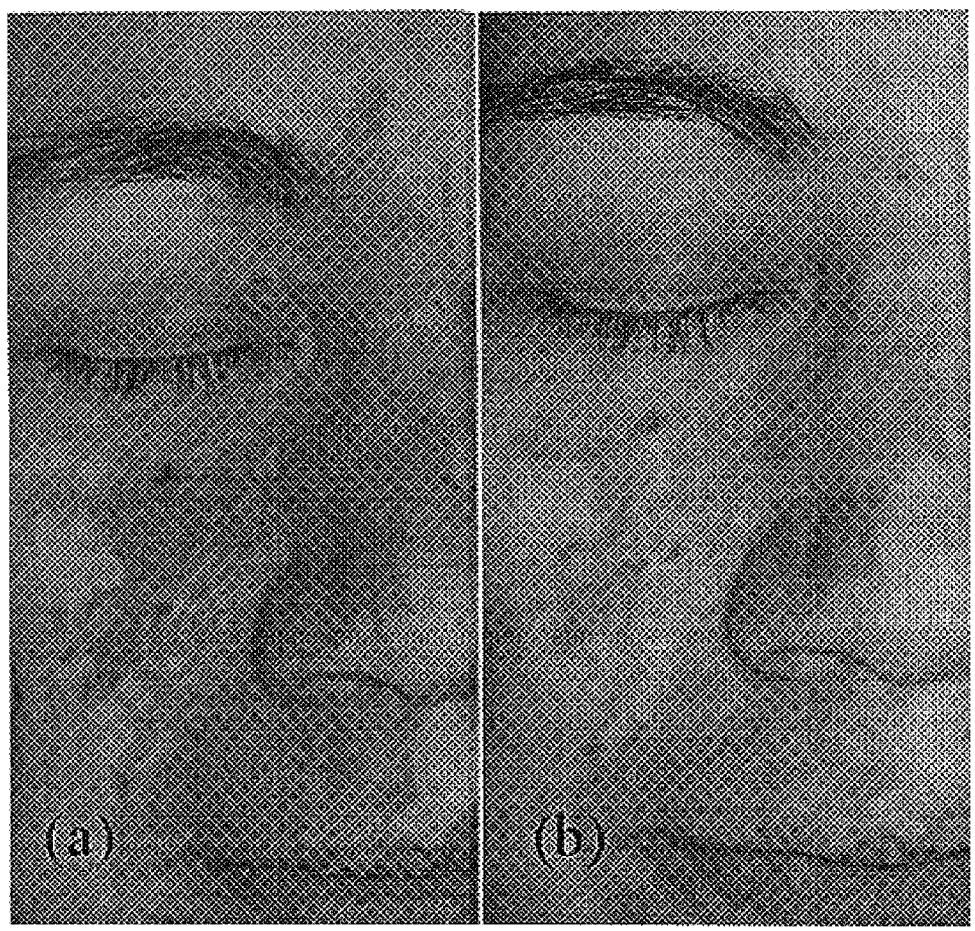
FIG. 6a is a digital cross-polarized RGB image taken of a patient prior to treatment.
FIG. 6b is a digital cross-polarized RGB image taken of a patient prior to the subsequent treatment. Qualitative evaluation of the PWS indicates substantial reduction in red color saturation.
Figures 7A, 7B:
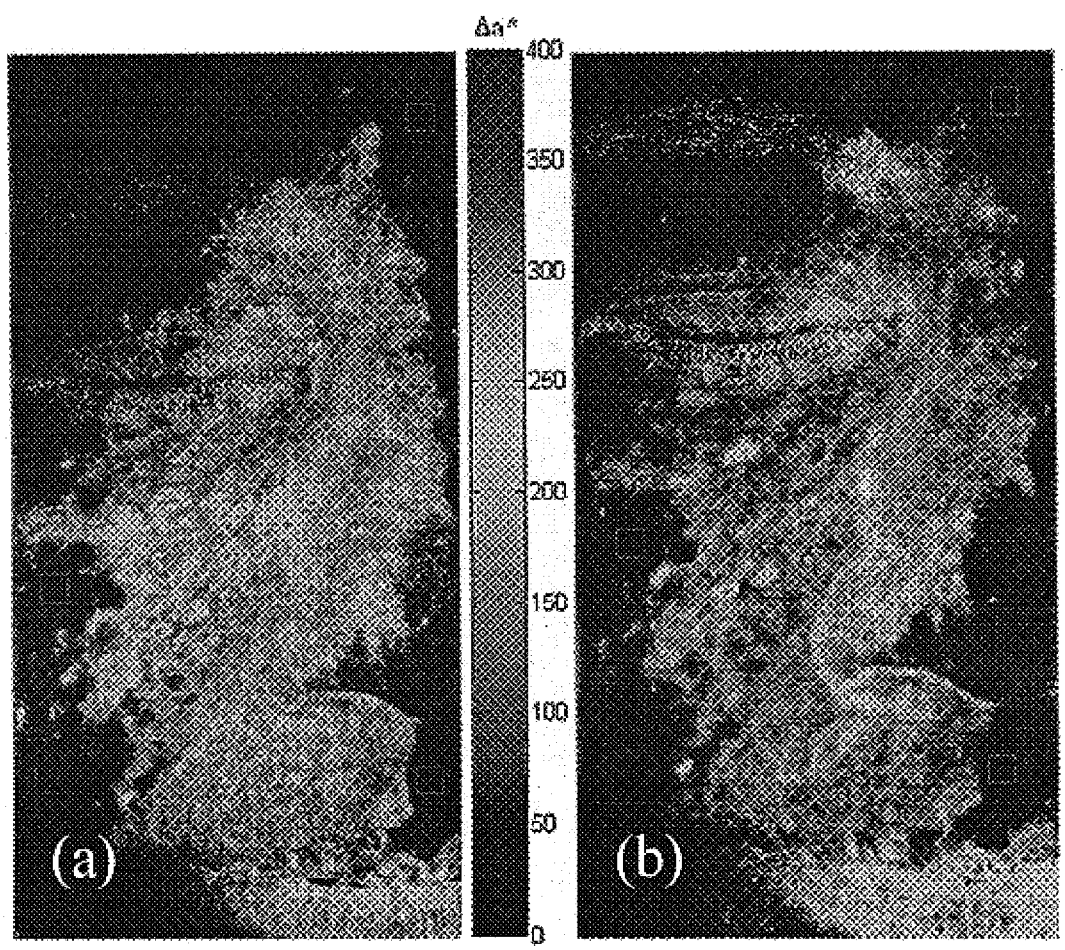
FIGS. 7a and 7b are $\Delta a^*$ images computed from RGB images shown in FIGS. 6a and 6b respectively. The three red squares in each image demarcate selected regions of normal skin. The light blue colored region (e.g., $\Delta a^*$ equals ~150%) is fairly uniform in FIG. 7a and patchy in FIG. 7b. In the latter image, several subregions of light blue color have become darker blue (e.g., $\Delta a^*$ equals ~50%), indicating local subregions of reduced erythema.
Figure 8A:
FIG. 8a is a digital cross-polarized RGB images taken of a patient prior to treatment.
Figure 8B:
FIG. 8b is a digital cross-polarized RGB images taken of the same patient 2 months after treatment. Qualitative evaluation of the PWS indicates no substantial change.

For objective evaluation of PWS therapy, a RGB image of a patient's PWS can be taken with each visit as shown in FIG. 7a. Corresponding L* and a* images of FIGS. 5b and 5c can be computed. Ideally, the patient's head would be positioned in an identical location each time, allowing for direct pixel by pixel comparison of L* and a* images from successive visits. However, although the custom head/chin rest of FIG. 4 allows for repeatable positioning of the head during an imaging session, it is not possible to control all degrees of freedom (e.g., vertical/horizontal tilt). To normalize each L* and a* image for direct comparison among visits, a relative a* image (Δa*) can be computed. A relative a* index difference image, Δa*, was computed using the equation (3):

$$\Delta a^* = 100\left(\frac{a^*_{PWS} - a^*_{NS}}{a^*_{NS}}\right) \quad (3)$$

where $a^*_{PWS}$ represents the raw a* indices in the image and $a^*_{NS}$ the average a* indices of representative regions of normal skin selected near to the PWS. Thus, Δa* represents the relative difference of erythema of PWS skin to that of normal skin at each pixel in the image. With each visit, a reduction in PWS lesion severity can be quantified by directly comparing Δa* values. FIGS. 6a and 6b are photographic images of the patient of FIG. 5a prior to treatment and after initial treatment respectively. FIGS. 7a and 7b are the Δa* images corresponding to FIGS. 6a and 6b.

Figure 9A:
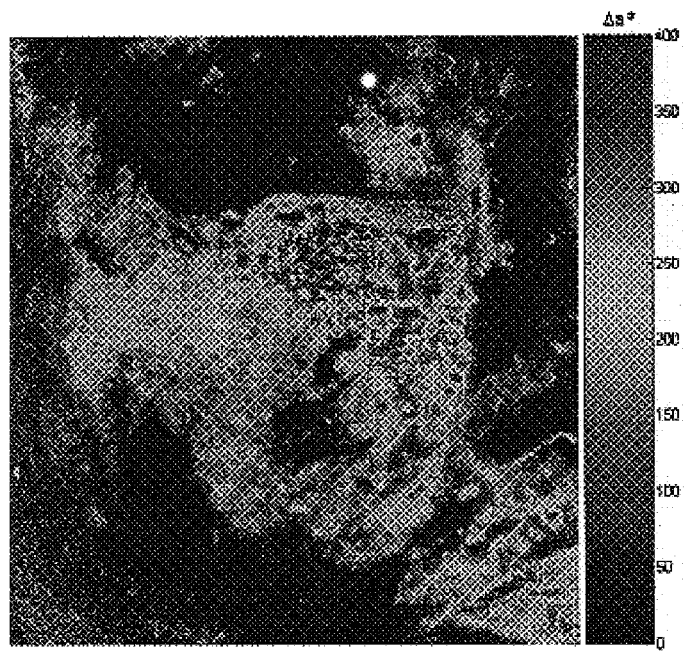
FIGS. 9a and 9b are the $\Delta a^*$ images computed from RGB images shown in FIGS. 8a and 8b respectively. Note a pronounced difference between before laser treatment in FIG. 10a and after in FIG. 10b.
Figure 9B:
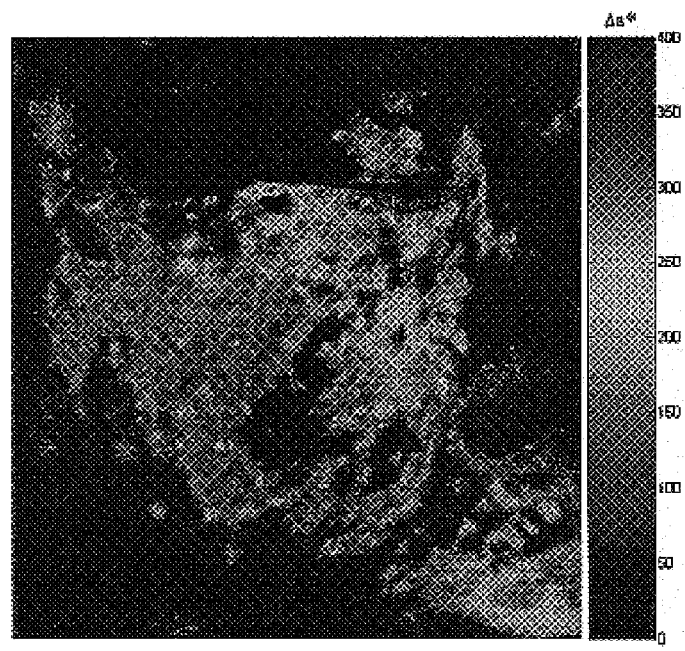

FIGS. 8a, 8b, 9a and 9b depict an identical analysis for a PWS patient for whom the crossed-polarizer image alone seems to indicate that the port wine stain lesion is not responsive to therapy. FIGS. 9a and 9b however indicates that, based on Δa* values, there are changes in the lesion that are not apparent in the RGB image. The object of the invention is to ensure that this result is rigorously characterized by the system 10 and the method of the invention to ensure that result is not an artifact.

In the quantitative evaluation of facial skin chromophore content (melanin and hemoglobin) using color imaging, several factors affect the accuracy of measured values, such as view angle and facial curvature. To determine the influence of view angle and facial curvature on the accuracy of quantitative image analysis, cross-polarized diffuse reflectance color images of a mannequin head model and human subjects are used while varying the angular position of the head with respect to the image acquisition system. The results indicate that view angle and facial curvature influence the accuracy of the recorded color information and quantitative image analysis. Moreover, there exists an optimal view angle that minimizes the artifacts in color determination resulting from facial curvature. From this analysis, optimal view angles are identified to image specific regions of interest on the face of human subjects.

Since most PWS lesions occur on the face, it is necessary to characterize the influence of the facial surface curvature and view angle of the camera system on the color values derived from the images. To examine the effects of such variables on quantitative image analysis, we conducted experiments using a mannequin head model and one PWS human subject. We disclose here a procedure that minimizes the effects of facial curvature and view angle on the accuracy of quantitative analysis of the chromophore (melanin and hemoglobin) content in human skin.

As described in connection with FIG. 2 the imaging system 10 uses a Minolta Dimage 7 digital camera 12. The system 10 incorporates an AC-adapter powered ring flash 18 for consistent uniform illumination. Cross-polarized optics or analyzer 14 were used to remove surface glare, which corrupts subsurface skin color measurement. Using a Kodak gray card (not shown) (E152 7795, Tiffen, Rochester, N.Y.), the white balance and exposure of the digital camera 12 were manually adjusted to set the chromatic ratio at red (R)=128/green (G)=128/blue (B)=128. The optimized camera parameters were ISO 200, aperture size F/8, shutter speed 1/60s, and flash intensity level of 1/2.

Figure 10:
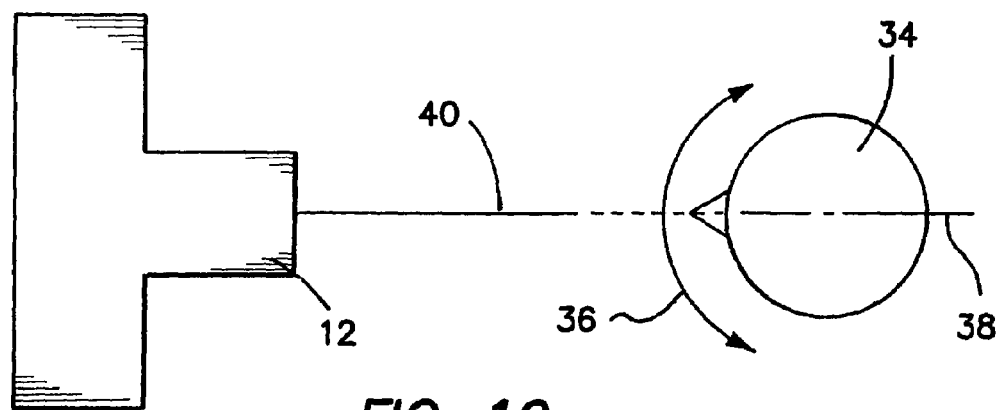
FIG. 10 is a top plan view diagram of facial image acquisition showing the view angles, defined as the angle between the optical axis of the imaging system and medial facial plane, selected by adjusting the rotation of the head-positioning device.

To ensure that test sites on the face were positioned in a reproducible manner, a custom head-positioning device 22 described above in connection with FIG. 4 was constructed and placed within the working distance of the ring flash 18, resulting in uniform illumination. The view angle for facial imaging was selected by rotating the head-positioning device 22 as indicated by the bidirectional arrow 36 in FIG. 10 and defined as the angle between the medial facial plane 38 and optical axis 40. The optimal view angle was defined as the view angle that minimized non-uniform illumination on the facial region of interest.

Using the same procedure described above, cross-polarized diffuse reflectance color images were converted into CIEL*a*b* color values. In the CIEL*a*b* color space, the reflected light intensity was quantified as L* and erythema (i.e., degree of redness) as a*. Lower L* and higher a* values are indicative of higher reflectivity and erythema values, respectively. For the color space conversion, the tristimulus X, Y, and Z images of the sample (skin) and calibration reference were first calculated from respective cross-polarized diffuse reflectance color images using the $D_{65}$ conversion matrix (Equation 1 above). As a calibration reference, RGB values for a 99% diffuse reflectance standard (Model SRT-99-100, Labsphere, North Sutton, N.H.) were measured yielding the matrix shown in equation (1) above. Tristimulus images for the samples (X, Y, Z) and calibration references ($X_n$, $Y_n$, $Z_n$) were utilized to calculate tristimulus L*a*b* values using the following equations (2a)-(2f) above.

Ideally, light incident on the target area should be uniformly distributed for accurate quantitative image analysis. To investigate the influence of view angle on the uniformity of incident light distribution, a 99% diffuse reflectance standard (not shown) with a uniform flat surface of 30 cm² was placed in the head-positioning device 22. Cross-polarized diffuse reflectance images were acquired at view angles of 0 and 35°, which were assumed to be optimal and suboptimal angles, respectively. L* images for both angles were computed from the cross-polarized diffuse reflectance images.

Figure 11:
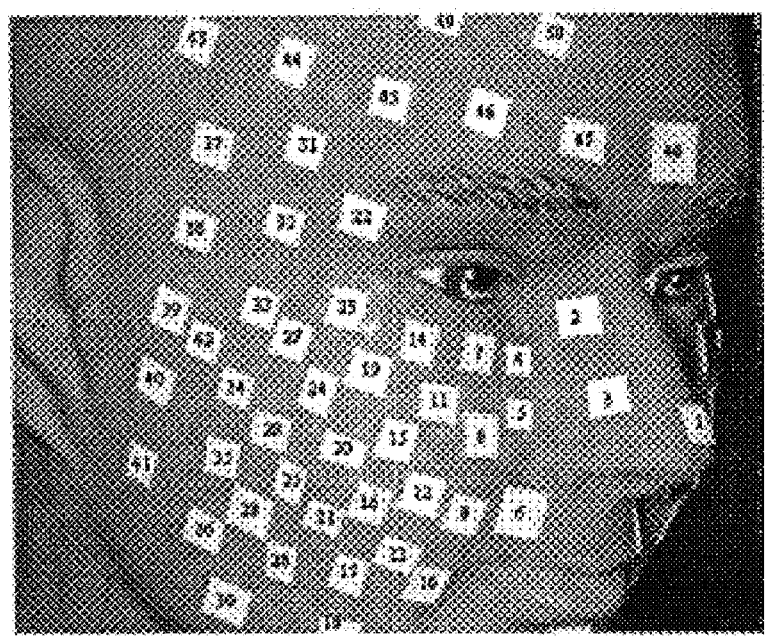
FIG. 11 is a photograph of a mannequin head model used to study the uniformity of the light distribution. Fifty white patches were positioned on the entire right side-face of the mannequin head. This image was acquired at a view angle of 45°.

The uniformity of light distribution due to facial curvature was studied with a physical mannequin head model, assuming that the mannequin face is representative of the shape of the human face. Fifty white patches (1 cm² area each) were removed from a Kodak gray card and positioned on the entire right side-face of the mannequin head model as depicted in the photograph of FIG. 11.

The mannequin head model was placed in the head-positioning device 22 and images were obtained from multiple view angles varying between 0 and 90°, inclusive, in increment of 10°. For each image, L* values of the patches were computed using equations 1 and 2a-2f. The optimal view angle was determined based on the average L* value and coefficient of variation (C.V.) of the selected white patches. Mean (µ) and standard deviation (σ) values of L* from different subsets of patches were computed and the C.V. calculated as follows:

$$C.V.(\%) = [\sigma/\mu] \times 100 \quad (3)$$

A lower C.V. indicates a lower dispersion in L* over the subset of patches and, therefore, a more uniform incident light distribution. The statistical analysis was performed using SPSS Version 8 (SPSS, SPSS Inc, Chicago, Ill.).

Figure 12A:
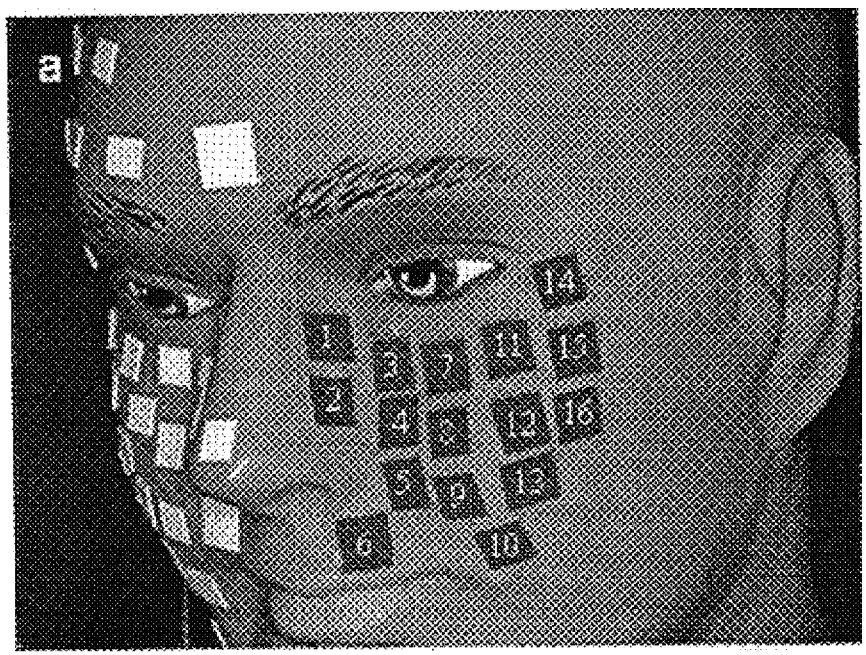
FIGS. 12a and 12b is a photograph of a mannequin head model and human subject respectively. The model of FIG. 12a was used to simulate a PWS birthmark, red patches were positioned on the mannequin head model of the human subject of FIG. 12b. Sixteen red patches were attached at similar locations on the mannequin head model and the human subject. Cross-polarized diffuse reflectance images were acquired at the optimal view angle of 35°.
Figure 12B:
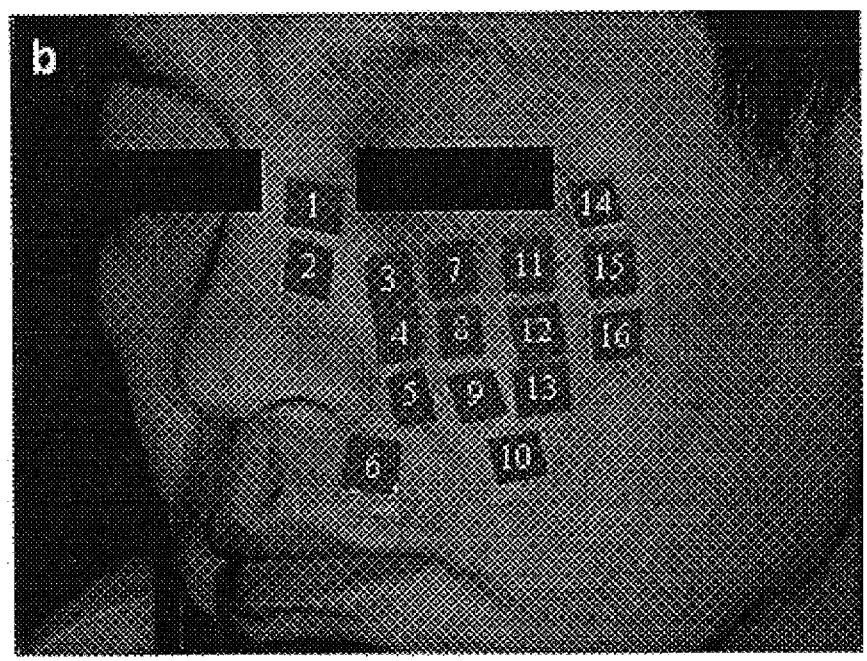

To simulate a PWS lesion, sixteen red color patches (1 cm² area each) from a Macbeth color checker were placed on the left side-face of the mannequin model in FIG. 12a and a human subject in FIG. 12b with normal skin. Every effort was made to replicate patch location on both the model and subject. From images of white patches placed at corresponding locations on the contralateral side of the model (i.e., patches 2-9, 11, 12, 14-16, 19, 20, 23, 24, and 27 in FIG. 12a), the optimal view angle to image the entire red patched region was determined from C.V. values determined. Using this optimal view angle, images of the red patches on both the model and subject were acquired and a* values determined.

The clinical relevance of view angle was investigated on a PWS patient receiving laser treatment at the Beckman Laser Institute at the University of California at Irvine. Images were acquired at two different suboptimal view angles and, then, respective a* image was compared to demonstrate the importance of view angle for quantitative image analysis. Three consecutive cross-polarized diffuse reflectance color images were acquired at the optimal view angle for the PWS lesion evaluated over an eight week period. Qualitative assessment was performed by comparing PWS skin color change in consecutive images. For quantitative assessment of PWS erythema, a* images were computed from the corresponding color images.

The optimized imaging system 10 provides a uniform light distribution on a flat surface. Using the selected camera parameters, a uniform light distribution on the 99% diffuse reflectance standard was obtained at a view angle of 0°. At a view angle of 35°, the resultant light distribution was nonuniform. To test system stability, images of the diffuse reflectance standard were acquired at a view angle of 0° on five separate days. RGB values (µ±σ) were 250±1.3, 252±1.7, and 251±1.2, respectively, demonstrating the stability of our imaging system.

Figure 13:
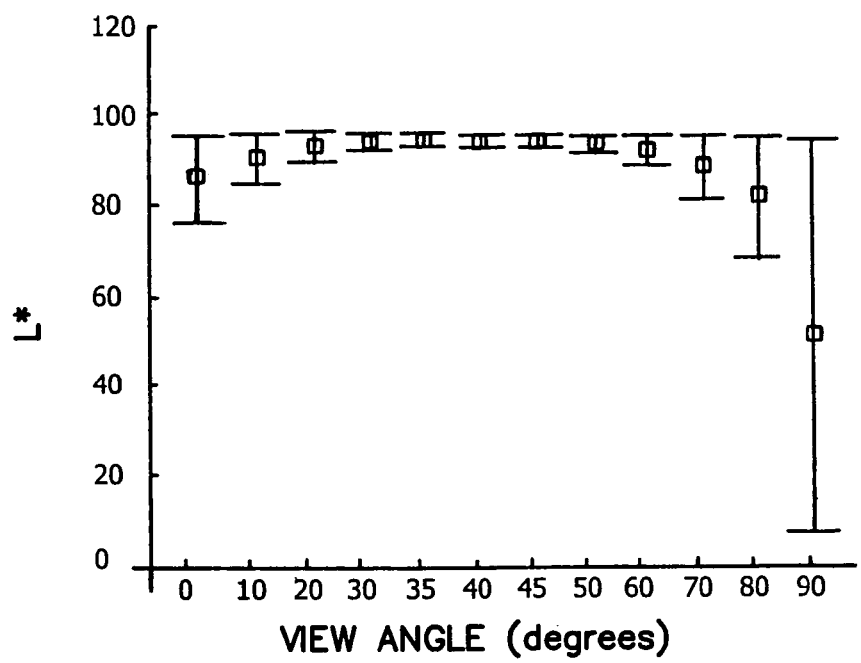
FIG. 13 is a graph illustrating the dependence of L* values on view angle. In this measurement, patches 2-21 comprised the region of interest, and the optimal view angle was determined to be 40° (C.V.=1.2%).

The optimal view angles depend on the region of interest. To simulate different region of interest on the face, optimal view angles were determined for different subsets of the fifty white patches placed on the mannequin head model. FIG. 13 illustrates the dependence of L* values on view angle for a region of interest covering primarily the front side of the face (i.e., patches 2-21 in FIG. 11. The C.V. is at a minimum (1.2%) at a view angle of 40°, suggesting that this is the optimal view angle. Based on the results shown in Table 3, the optimal view angle varies and should be determined based on the region of interest under study.

TABLE 3

Summary of optimal view angles for imaging different regions of interest of the mannequin head model (FIG. 11).

| Location Numbers | Optimal View Angle (degree) | C.V. (%) |
|---|---|---|
| 1-50 | 40 | 2.86 |
| 2-42 | 50 | 1.97 |
| 2-21 | 40 | 1.2 |
| 19-42 | 70 | 0.3 |

Use of the red patches to simulate a PWS lesion resulted in similar results for both the mannequin head model and human subject with normal skin. From the white patched mannequin head model data shown in FIG. 14, the optimal view angle for the red patched region was determined to be 35° (C.V. 0.39%). At the optimal view angles, the mean a* values of the red patches on the mannequin model and human subject with normal skin were 37.47±0.63 (C.V. 1.6%) and 40.64±0.78 (C.V. 1.9%), respectively. From the image of the red patches at a 0° view angle, the mean a* value was 38.98±0.67 (C.V. 1.71%). The a* values of the simulated PWS lesion on the human subject with normal skin were higher than those from the mannequin head model.

Figure 15A:
FIGS. 15a and 15b are photographs of a PWS patient using cross-polarized diffuse reflectance color and a* images taken at view angles of 20° respectively.
Figure 16A:
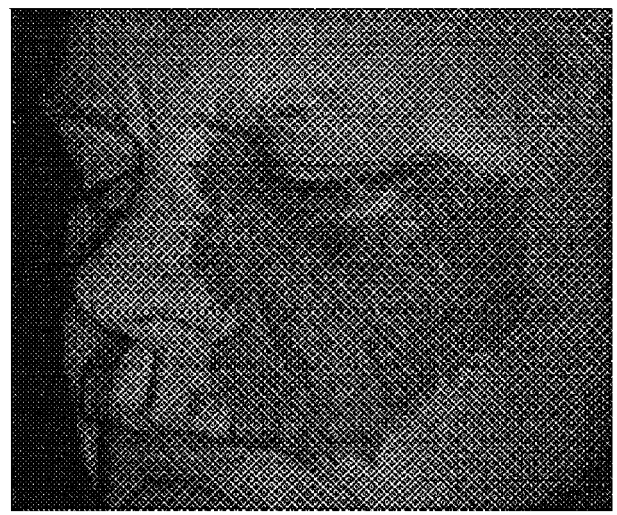
FIGS. 16a and 16b are photographs of a PWS patient using cross-polarized diffuse reflectance color and a* images taken at view angles of and 40° respectively. In both FIGS. 15b and 16b an angular artifact in quantitative assessment of a* was emphasized in the region of interest enclosed in the solid black line, in which the a* value distributions are different.
Figure 15B:
Figure 16B:
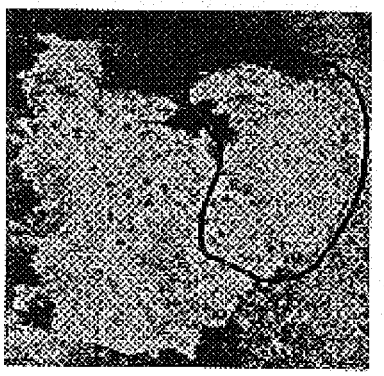

The view angle affects the quantitative assessment of PWS skin erythema. At the same patient visit, two cross-polarized diffuse reflectance images were obtained at view angles of 20° (FIG. 15a) and 40° (FIG. 16a) and the corresponding a* images were computed (FIGS. 15b and 16b respectively). The region enclosed by the black line illustrated different a* distributions compared to the other region. Using the C.V. based analysis described above, the optimal view angle to image the PWS lesion was determined to be 45°. Over an eight week period, three cross-polarized diffuse reflectance color images were obtained from the same patient (FIGS. 17a-17c, left side) at a view angle of 45°. Qualitatively, it appears that on the contrary of normal area presenting quasi-constant skin color, red skin color in PWS lesion was gradually lighter in subsequent images due to the laser treatment effect. Such variation of erythema in normal and PWS lesion was emphasized in quantitative a* images of corresponding color images as shown in FIGS. 17a-17c, right side. In the color bar, higher a* value means higher erythema.

Figure 14:
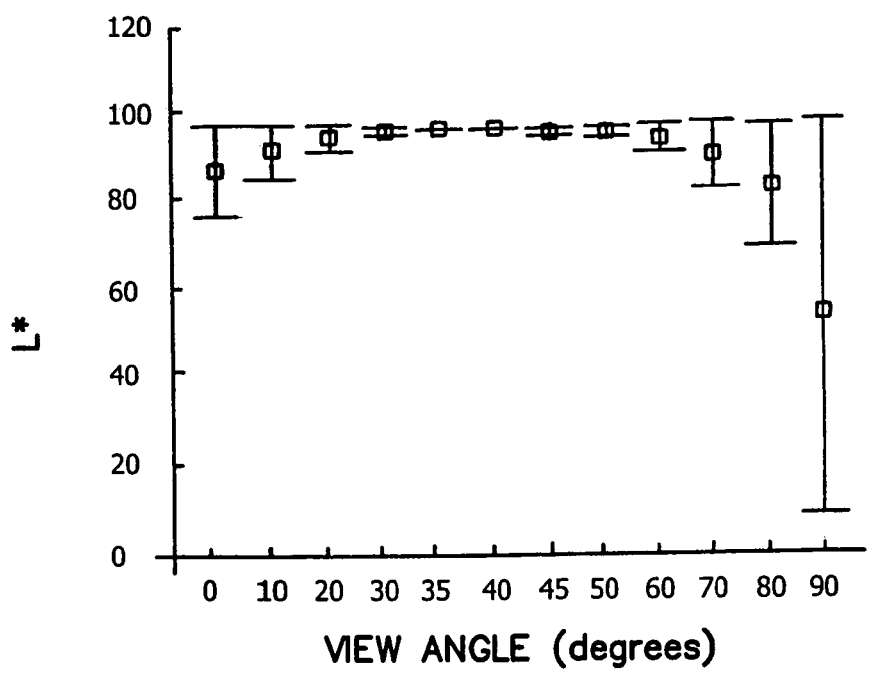
FIG. 14 is a graph illustrating the effect of view angle on L* in the white patch region of interest corresponding to the PWS-simulating red patches on the mannequin head model. The white patches corresponding to the red patches were 2-9, 11-12, 14-16, 19-20, 23-24, and 27. The optimal view angle was 35° with a C.V. of 0.4% ($\mu$:95.87 & $\sigma$:±0.4).

The results indicate that surface curvature and view angle affect quantitative measurements of facial skin color. The distributions of reflected light from a 99% diffuse reflectance standard acquired at two view angles demonstrated that view angle affects the uniformity of the incident light distribution. The variation in C.V. with view angle showed that an optimal view angle exists for a given surface curvature (FIGS. 13 and 14). In both cases, variations in C.V. are relatively insensitive to view angles of ±10° from the selected optimal view angles. However, in clinical practice, it is obvious that reproducing head position at each patient visit is essential. Finally, evidence that view angle affects quantitative image analysis is that images acquired from the same subject from two view angles possessed noticeable difference in a* values on the higher skin curvature region compared to the relative flat region (FIGS. 15a, 15b, 16a, 16b). Such angular dependent light distribution, if optimal view angle is not used, also causes error in site-by-site comparison of PWS treatment results in each treatment due to the nonuniform light distribution on the PWS lesion.

A surprising finding was that the a* values of the simulated PWS birthmark on the human subject were higher than those from the mannequin head model even though the a* values were expected to be the same because the red patches on both cases are identical. We believe that this difference is attributed to differences in vertical tilt between the human subject and mannequin head model and to slight differences in placement of the red patches. In a separate experiment, red patches were placed on a flat panel, and the vertical tilt was changed from 0° to 10°. Resultant a* values determined from the cross-polarized diffuse reflectance images were different by approximately two (38.5 vs. 40.2 at 0° and 10°, respectively). Therefore, to maximize the accuracy of quantitative analysis determined from cross-polarized diffuse reflectance images, it is necessary to use a head-positioning device with adjustments for both vertical and horizontal tilt.

Results obtained with the mannequin head model (FIG. 13) and human subjects with normal (FIG. 14) and PWS skin (FIGS. 15a, 15b, 16a, 16b) demonstrate the importance of considering the region of interest in facial imaging. As shown in Table 3, the optimal view angle depended on the region of interest. Furthermore, the C.V. was higher when a relatively large region of interest was selected (e.g., patches 1-50) as compared to when a smaller region of interest was considered; this was due to the higher degree of nonuniformity in the illumination over the larger region of interest due to local differences in facial curvature. This result is comparable to those obtained by others who determined that when a region of interest was close to the region used for color calibration, the error was minimized. Therefore, we recommend that facial imaging should be performed at multiple view angles, and the optimal view angle determined individually for different regions of interest. This recommendation allows for direct quantitative comparison of images obtained at different patient visits to monitor the progress of PWS laser therapy throughout an extended treatment protocol (FIGS. 17a, 17b and 17c).

In summary, the uniform light distribution in target area was critical issue for accurate quantitative and qualitative comparison of preoperative and postoperative result. That issue was studied with the white patched mannequin head model and the digital imaging system built in laboratory. The white patched mannequin head model was turned out to be effective in flexible determination of optimal view angle depending on target area (ex, PWS lesion), minimizing error related to the non-uniform light distribution. Using optimal view angle in image acquisition also minimized error in a* computation that is quantitative mapping of erythema, presenting clinical feasibility of white patched mannequin head model in real PWS patient.

The foregoing results demonstrate that crossed-polarizer digital imaging system provides semi-quantitative information on melanin and erythema. It must be understood that the scope of the invention includes optimization of system 10 to determine the optimal melanin and erythema metrics to use and to objectively evaluate patient progress during the course of PWS laser therapy. The intended use of system 10 contemplates the general capability of recovery of chromophore content in skin.

It is also to be understood that components can be optimized and the sources of variation systematically characterized. Several factors affect the quality of information contained in each digital image. For example, the crossed-polarizer illumination/detection configuration can be selected to provide high discrimination between the specularly reflected light from a surface and diffuse, multiply scattered subsurface light, conferring to an imaging system a certain degree of "optical sectioning". Polarizing optics with different crossed polarizer extinction specifications (e.g., $10^{-2}$ vs. $10^{-3}$) can be tested to empirically determine the effect of extinction ratio on image analysis. Related to this, the system can be tested with polarizing elements in place and the crossed-polarizer extinction of the polarizing elements in the system 10 compared to the crossed-polarizer extinction of the elements tested alone. The objective of this test is to verify that there are no components in the optical train of the imaging system that possess birefringent properties that would significantly alter the polarization state of the light passing through the system 10.

Furthermore, the sensitivity of the images and analysis method to small angular perturbations of the polarizer with respect to the analyzer can be determined in order to characterize the effects of small misalignment on the results. This is done by purposely and methodically displacing the angular position of the polarizing elements with respect to the other.

Still further, the camera system is designed to allow for variation of different settings to achieve the best possible white balance for a given set of lighting conditions. Images are taken using the macro ring flash as the illumination source. Camera parameters such as shutter speed, aperture, and light intensity can be varied systematically to identify the best combination of each parameter for achieving ideal white balance. To optimize image contrast, a gray card (Grey Card Plus, Eastman Kodak Company, Rochester, N.Y.) can be imaged. Ideally, the response of each pixel should be 128 for each of the RGB color channels. Five gray card images could be acquired for each set of parameters. Also, single images of a 99% diffuse reflectance standard are obtained. Normalized gray card images are determined by dividing each color channel by the corresponding channel in the reflectance standard image. Mean and standard deviations of normalized values in each gray card image are calculated to obtain a pixel map for each channel. An ideal map contains mean and standard deviation values of 0.5 and 0.0, respectively at each pixel. The pixel values with maximum and median deviations (e.g., deviation=mean+standard deviation−0.5) from these ideal values are identified and presented as such. This procedure is repeated periodically in order to characterize variations associated with usage related changes in the illumination source.

The effects of ambient lighting are optimizable. The feasibility of performing "flash" imaging in the presence of room lights can be tested. The system 10 should be configure to yield robust analysis in a clinical setting. This requires an understanding of the impact of ambient lighting on various commonly used image acquisition parameters and on the melanin and erythema indices that are deduced. Camera parameters such as shutter speed, aperture, and flash intensity are varied systematically both in the presence of room lights and in the absence of room lights to determine the feasibility of using this imaging approach on PWS in the presence of ambient lighting.

Image repeatability is optimized. To quantify the error associated with variations in image response due to detector noise or fluctuations with the macro ring flash, a Macbeth color checker card is imaged. Macbeth color checker cards contain multiple different colored patches that are considered as standard colors. Five images of each color patch are taken and mean and standard deviation values computed for each pixel. The overall mean and standard deviation ($m_{ir,i}$ and $\sigma_{ir,i}$, where "i" is a patch specific index) for each patch and each color channel is determined.

Overall error computation is performed to optimize system 10. After selection of camera parameters for optimizing white balance, overall system error is computed for different facial regions. From the mannequin head experiment, a single mean and standard deviation value ($m_{cc,i,j,ang}$ and $\sigma_{cc,i,j,ang}$ respectively) is obtained for each color channel "cc", a choice of color "i", position "j", and angle "ang". Furthermore, by acquiring a set of five images, $m_{cc,i,j,ang}$ and $\sigma_{cc,i,j,ang}$ contain error associated with image repeatability as well. To determine the accuracy in determination of CIE L*a*b* values, standard error propagation techniques are used. Error formulas are applied in a stepwise fashion to determine first the overall error in calculation of XYZ tristimulus values using Equation 1, and then in calculation of L*a*b* values using Equation 2. Statistical error propagation analysis is used to determine the overall magnitude of multiple sources of error on CIE L*a*b* values computed from each RGB image. Whenever possible, steps are taken to minimize the associated error.

System 10 is validated against appropriate "gold-standard" systems. Reflectance measurements are acquired with crossed-polarizer digital imaging system 10 and a tristimulus calorimeter. Data is first acquired on non-tissue reference material to eliminate measurement error associated with contact-pressure-induced blanching of skin. A Macbeth color checker is used as the object. A comparison is drawn between L*a*b* values measured with the two devices.

Replicate RGB images of a specific color patch on the checker are acquired. Without moving either the camera 12 or the checker, a tristimulus calorimeter (CR-200, Minolta Corp.) is placed on the same patch. The calorimeter output is a single set of L*a*b* values averaged over the interrogated area. Replicate measurements are obtained in which the colorimeter is lifted and replaced as close to the exact position as possible. A marker will be used to trace the outline of the colorimeter aperture directly on the checker. The calorimeter will be removed and a RGB image acquired to determine the exact region interrogated with the colorimeter. During post processing, each pixel in the interrogated region of each image is converted from RGB to L*a*b*. With a t-test (95% confidence interval), these values are compared to those measured with the colorimeter to determine the correlation between the two sets of data. The calorimeter and digital imaging system 10 are seen to provide statistically similar measures of L*a*b*, demonstrating the potential of system 10 to provide clinically useful images in the L*a*b* color space.

Clinical data is acquired and analyzed to further validate the system 10. In a single year, between 100 and 150 patients are treated for PWS at the Laser Surgery Clinic associated with BLI at the University of California. Many of these patients undergo 3-4 treatments per year, depending on age, speed of recovery and response to treatment. Images from between 20-30 of these patients are acquired per year. Measurements taken with our system are compared to subjective evaluation provided by two clinicians at BLI. Age, sex, skin type, PWS anatomic location and severity score pre-laser treatment are extracted and stratified from the chart.

Prior to laser treatment, the head of each patient is placed in the custom head/chin rest 22. Crossed-polarizer digital images are acquired at multiple angles. The selection of imaging angle will depend on PWS anatomic location. For example, a PWS on the cheek may be imaged at 0° (e.g., front view) and 45°. An image of a 50% diffuse reflectance standard is also obtained to provide an alternate reference standard. All system parameters are recorded. At each subsequent visit, the same system parameters are used to maximize our ability to quantitatively compare images taken at different visits.

Each RGB image is converted to L*a*b* color space and the optimal melanin and erythema metrics calculated. From the erythema metric image (e.g., E or a*), a relative erythema metric image is determined (e.g., $\Delta$E or $\Delta$a*) as described below. This image is compared with corresponding $\Delta$E or $\Delta$a* images taken at subsequent visits. Five sites are identified in each image, and a Mean Blanching Score (MBS) is computed as follows (using $\Delta$E as an example):

$$MBS = \frac{\sum_{i=1}^{5}(\Delta E_{i,j+1} - \Delta E_{i,j})}{5} \quad (4)$$

where $\Delta E_{i,j}$ is the mean $\Delta$E value determined at site "i" and at visit "j".

Subjective clinical evaluation of PWS sites are performed, both in real time while the patient is present, and using standard, non-polarized photography, by two laser surgeons with considerable experience in PWS patient management. The following Clinical Blanching Scores (CBS) are assigned to evaluation of the crossed-polarizer digital RGB images: 0=less than 25% blanching, 1=25-49% blanching, 2=50-74% blanching, and 3 greater than 75% blanching [34]. MBS and CBS scores are compared and linear regression analysis applied to determine the ability of the crossed-polarizer digital images to quantify blanching of PWS lesions in a similar fashion to experienced clinicians.

It is also to be understood that the algorithms for deducing melanin and erythema related indices can be optimized. Several measures of melanin and erythema have been proposed in the literature. Both direct and indirect evidence has been presented to support each of the metrics. Each index provides an accurate representation of melanin or hemoglobin. Previous studies have shown that a given set of melanin and erythema metrics may not provide independent measures of melanin and hemoglobin, respectively. Regions of high (low) melanin content can result in measurements of artificially low (high) hemoglobin content. Since PWS skin can have a high degree of erythema, this lack of independence is a relevant issue. Digital imaging system 10 is used to determine the correlation between different melanin and erythema metrics to identify the best combination to use for evaluation of patient response to PWS laser therapy.

Images of a select group of patients undergoing laser therapy at the Surgery Laser Clinic in BLI are acquired. Each image is converted from the RGB to L*a*b* color space using Equations 1 and 2. The following melanin metrics are determined: L*, b*, melanin index (M), b*/L*, and $\alpha$, where $$M = 100 \log_{10}(1/R_g) \quad (5)$$

$$R_g = \frac{R_{skin,g}}{R_{rs,g}} \quad (6)$$

$$\alpha = \tan^{-1}\left(\frac{L^* - 50}{b^*}\right) \quad (7)$$

where $R_g$ is the percent reflectance of the green color channel, $R_{skin,g}$ is the green channel pixel value measured on skin, and $R_{rs,g}$ is the green channel pixel value measured with a 99% diffuse reflectance standard. The following erythema indices are determined: a* and erythema index (E), where $$E = 100 \log_{10}\left(\frac{R_r}{R_g}\right) \quad (8)$$

where $R_r$ is the percent reflectance of the red color channel and is calculated in a similar fashion to $R_g$.

Correlations among melanin and erythema metrics are investigated by applying linear regression principles. Correlation coefficients (r and $r^2$) are calculated to determine the degree of correlation between a given set of two metrics. To ensure that linear regression analysis is justified, bivariate scatter plots and the Kolmogorov-Smirnov test are used to identify nonlinear components and test the implicit assumption of normality, respectively. With this analysis, we identify the optimal combination of melanin and erythema metrics to provide relatively independent quantitative measures of melanin and hemoglobin, respectively. This combination will be used for analysis of images acquired from PWS patients as described above.

What results from the foregoing optimizations is a crossed-polarizer digital imaging system that can be used in the clinic to quantify blanching of PWS lesions. We have optimized system parameters and quantified the error associated with variables such as imaging angle. We have determined an optimized set of melanin and erythema metrics to use in subsequent image processing steps. One use of the system is to guide clinicians in management of PWS patients. For example, patients who are minimally responsive to laser therapy can be identified. With these patients, a different course of laser therapy (e.g., alternative laser wavelength) can be designed, or treatments can be stopped altogether. This system, as fully characterized and developed, has the potential to improve the safety and efficacy of PWS laser therapy in the near future.

In summary, system 10 gives similar results to a tristimulus calorimeter, the selection of melanin/erythema metrics is justified, and has shown good correlation between Mean Blanching Scores (MBS) and Clinical Blanching Scores (CBS) from patient measurements. Specifically, we have:

1. Thoroughly characterized system 10 in terms of sources of variation and sensitivity to these sources. We have determined the sensitivity of the analysis to the quality of crossed-polarizer extinction, identified the optimal system settings for achieving the best white balance possible. We have experimentally determined the error associated with variations among "identical" images (e.g., image repeatability) and with angle. We have calculated overall system error for determination of L*a*b* color values.
2. Established the degree of correlation between L*a*b* color values determined with a non-imaging tristimulus colorimeter and digital imaging system 10.
3. Determined the optimal set of melanin and erythema metrics to use for evaluating RGB images taken from PWS patients.
4. Acquired and processed RGB images from PWS patients during three separate visits. We have evaluated RGB images to determine CBS. We have calculated MBS from each erythema image. MBS and CBS scores are compared and linear regression analysis applied to determine the ability of the crossed-polarizer digital images to quantify blanching of PWS lesions in a similar fashion to experienced clinicians.

What results is a camera system which is a low cost medical imaging device capable of determining noninvasively chromophore content in skin, namely an optimized a low-cost crossed-polarizer digital imaging system for characterization of PWS skin response to laser therapy. Melanin and erythema metrics measured with the system and appropriate image processing provide qualitative information on relative melanin and hemoglobin content. This system 10 and the application of the methodology of the invention to PWS therapy results in a low-cost yet effective tool that has the potential for widespread use in objective evaluation of current therapeutic protocols.

The imaging system 10, with appropriate modification, can also be used for alternate applications, including assessment of treatment endpoints of narrow band UV-B and XeCl based psoriasis therapies and as a tool to assist in discriminating between various types of skin cancer and benign skin pathologies. Knowledge of absolute values of chromophores such as melanin and oxy- and deoxy-hemoglobin can serve as an objective indicator of disease progression in skin. With a series of controlled experiments, system 10 can be further refined modified to recover absolute chromophore content in skin.

The imaging system 10 of the invention includes within its scope modification to expand its capabilities to quantify chromophore content in skin. Forward computational models are designed and employed to simulate reflectance spectra of skin with varying melanin content, blood vessel size, vessel number density, total hemoglobin and blood oxygen saturation. Sensitivity analysis allows us to select the best wavelength ranges to study through informed selection of optical filters to test in our imaging system. The imaging system is appropriately modified to accommodate multiple optical filters to provide an inexpensive spectral imaging solution. Skin phantoms are constructed to test and validate the ability of our system to quantify chromophore content in heterogeneous layered turbid systems. Models of light propagation are subsequently be tested and optimized for appropriateness to solve the inverse problem of recovering chromophore content from reflectance spectral images.

Thus, it is to be understood that the invention contemplates modifications to:
1) Employ forward modeling to estimate sensitivity of particular wavelength bands. We employ a forward modeling based approach to identify the optimal wavelength bands to use for quantification of each chromophore of interest. Acquisition of reflectance data in specific wavelength bands maximizes our ability to quantify local melanin, oxyhemoglobin ($HbO_2$), and deoxyhemoglobin (Hb) content. Previous studies describe the effect of different chromophore quantities on reflectance spectra. However, results of these studies are of limited applicability to imaging system 10 due to use of oversimplified skin geometries in the models. We employ a sophisticated optical model with which we can systematically vary chromophore content, depth, and distribution to identify optimal wavelength bands to interrogate with system 10.

2) Validate instrumentation and modeling on appropriate test systems. Corollary to the development of enhanced imaging instrumentation and modeling tools, we design and construct tissue phantoms so that they possess characteristics that mimic the layered geometries and spectral properties of tissues of interest. Phantoms can be created in which absorption and scattering coefficients are precisely controlled and the concentrations of the chromophores pre-determined depending on which spectral regions we choose to focus on. This enables us to iteratively test both the wavelength band selection and the imaging geometry to determine absolute chromophore content in samples with known composition. In addition, this provides us the capability to quantitatively validate forward and inverse computational models.

3) Determine appropriate inverse models for deducing chromophore content from spectral images. Light transport in the spectral window between 650-1000 nm is dominated by scattering in most tissues. Outside of this range, absorption can be pronounced, with the effect of rendering diffusion approximation invalid. The models that we use to interpret in-vivo spectral tissue data accurately describe light propagation for short source-detector separations, highly absorbing and layered regimes.

4) Modify the crossed-polarizer imaging system to include spectral imaging capability. Sensitivity analysis of modeling and phantom data allows us to make informed selection of optical filters to test in our imaging system. The imaging system is appropriately modified to accommodate multiple optical filters in order to provide an inexpensive spectral imaging solution. We use the methodology of the invention to predict chromophore content on phantoms with non-imaging spectroscopy.

5) Spectroscopically validate chromophore content obtained from images. We utilize investigations in the area of quantitative tissue spectroscopy at short source-detector separations. The fiber-based spectroscopic technology which is part of Laser Microbeam and Medical Program (LAMMP) core technology is employed as a means for quantitative validation of tissue characteristics, such as Hb and $HbO_2$, that are correlated to the data determined with the imaging system 10. In particular, areas of PWS skin that have been imaged are also probed using Steady-State Frequency Domain Photon Migration (SS-FDPM). The existing SS-FDPM system is modified as part of the technology development program proposed in LAMMP. The probe source-detector separation is reduced to make the measurement amenable to the depth of the target tissue of interest. By this time, the wavelength range of the current SS-FDPM system, which currently operates in the range 650-1000 nm, is extended from 400-1000 nm. Optical properties obtained from skin phantoms and from in-vivo skin using this spectroscopic approach are compared to those obtained with our spectral imaging system.

The invention is thus a low-cost spectral imaging system to determine chromophore content of a skin phantom model. The physician can use system 10 as a tool to easily identify objectively local sites of abnormally high or low melanin or hemoglobin content. The clinician uses this information to make an informed decision on diagnosis of various skin conditions (e.g. psoriasis, skin cancer) or evaluate response to therapy (e.g. laser treatment of PWS, psoriasis, etc).

A series of experiments are described below that establish the ability of our crossed-polarizer digital imaging system 10 to measure chromophore content in turbid samples. These experiments include the following.

1. Employment of Forward Modeling to Optimize Selection of Wavelength Bands.

Acquisition of reflectance data in specific wavelength bands maximizes our ability to quantify local melanin, oxyhemoglobin ($HbO_2$), and deoxyhemoglobin (Hb) content. Previous studies describe the effect of different chromophore quantities on reflectance spectra. However, results of these studies are of limited applicability to imaging system 10 due to use of oversimplified skin geometries in the models. A more sophisticated optical model needs to be employed to identify optimal wavelength bands for incorporation into imaging system 10.

In the model, we systematically vary chromophore content, depth, and distribution. Melanin content varies between 2 and 8%, representative of skin color ranging between fair (e.g. Caucasian) and relatively dark (e.g., Asian) [40-42]. Total hemoglobin concentration varies within a normal range of 130 to 180 g/L. Oxygen saturation (e.g., ratio of $HbO_2$ concentration to total hemoglobin concentration) varies between 75 and 100%. Two sets of biopsy defined skin geometries are analyzed to determine blood vessel diameter and depth distribution in PWS skin. For normal skin, blood vessel diameter and fraction are set at 10 µm and 1%, respectively.

A Monte Carlo model is used to simulate light transport in skin. For a given set of chromophore values and distributions, we convert the initial geometry to a 1-D layered approach. Briefly, the geometry is divided into layers of epidermis, bloodless dermis, and dermis with vessels. Optical properties are assigned to epidermal and bloodless dermis using values from the literature. Absorption coefficient of dermis with vessels is calculated using knowledge of blood fraction and a correction factor. With a given set of optical properties, the reflectance spectrum over the visible (400-700 nm) range is computed for a total of 61 model runs per set. A parametric study is performed to determine the minimum number of photon packets required to maximize modeling efficiency. In the study use of 10,000 packets was sufficient. Reflectance spectra is calculated and analyzed to determine wavelength bands over which the spectra show maximum sensitivity to changes in a single chromophore.

2 Validate Instrumentation and Modeling on Tissue Phantoms

We experimentally verify the modeling results. This requires design and construction of realistic skin phantoms with known optical properties. The skin phantoms are comprised of polyacrylamide gel layers. Gel layers as thin as 100 µm can be made in a repeatable fashion. Epidermal layers are created by combining polyacrylamide components with synthetic melanin and Intralipid™, which is a scattering liquid used commonly in biomedical optics experiments. Dermal layers are comprised of polyacrylamide components, synthetic hemoglobin, and Intralipid. Sufficient Intralipid is added to all layers to achieve a scattering coefficient of 200 $cm^{-1}$, typical of skin. A thin layer of saline is applied between layers to ensure adequate optical contact between successive layers.

We use synthetic melanin and hemoglobin that is commercially available. Appropriate quantities of melanin and hemoglobin is used to achieve contents of 2-8% and 0.13-0.18 $g/cm^3$, respectively. To convert $HbO_2$ to Hb, sodium dithionite is added to select solutions of the former. Hemoglobin depth distributions is similar to those used in the Monte Carlo model described above.

To confirm optical properties of phantoms, spectrophotometric measurements of reflectance and transmittance are acquired using a Cary 5000 UV-Vis-NIR system with integrating sphere and an inverse adding-doubling algorithm to determine absorption and reduced scattering coefficients. This system is used to deduce broadband scattering and absorption properties so that the imaging system 10 is validated on samples having known and well-controlled properties that mimic the tissues of interest. A procedure has been developed for testing the optical properties of non-scattering phantom constituents and scattering constituents separately and then verifying the integrity of the optical properties of the combined components.

To determine the ability of the phantom to represent skin, a measured broadband reflectance spectrum of each composite phantom is compared with a corresponding spectrum calculated using the Monte Carlo approach described above. Differences between the spectra exist, primarily due to errors in the phantom preparation procedure. We perform error propagation analysis to compute the total error expected in chromophore content values, optical properties, and reflectance spectra, and to determine whether this error source alone can sufficiently account for any differences in spectral line shapes.

Once the phantom reflectance spectra are demonstrated to be sufficiently similar to those of skin, we acquire broadband reflectance spectra with the spectrophotometer to determine wavelength bands over which the spectra show maximum sensitivity to changes in a single chromophore. This data will complement the modeling data obtained with our Monte Carlo model described above.

3. Determine Appropriate Inverse Models for Deducing Chromophore Content from Spectral Images.

Several light transport models have been proposed in the prior art to determine chromophore content with knowledge of a tissue reflectance spectrum. Each model differs in terms of underlying assumptions, model approach, and computation time. We rigorously compare the performance of different models for our application of determining actual melanin and hemoglobin content in skin with our imaging system 10.

Reflectance values calculated with our Monte Carlo model in the wavelength bands of interest is used as input to three inverse optical models: rigorous diffusion theory based model, simplified diffusion theory based model, and the delta P1-approximation of light transport. The signal-to-noise ratio of our computed values is varied by adding white noise to the computed values. Using these models and the computed reflectance values, melanin content and hemoglobin concentration are calculated.

For each set of reflectance values, chromophore content is calculated. The relative accuracy of the content determined with the three inverse models is established for each of the different skin phantom geometries. The sensitivity of calculated chromophore content to noise in the reflectance values is determined for each model. Using this quantitative approach, an optimized inverse model is identified and used in subsequent measurements from skin phantoms and patients.

Finally, while hemoglobin and melanin are assumed to be the only skin chromophores, we realize that other chromophores may be present in the skin, especially in pathologic conditions. In such a case, the approach described here can be readily adapted to include these chromophores. One such example is bilirubin, which has a broad absorption band at 460 nm, giving skin the characteristic yellow color of jaundice.

4 Modify the Crossed-Polarizer Imaging System to Include Spectral Imaging Capability The imaging system is appropriately modified to accommodate multiple optical filters in order to provide an inexpensive spectral imaging solution. Use of the various filters allows for acquisition of band-limited images in wavelength bands selected specifically to provide maximum contrast in determining the content of each chromophore. Sensitivity analysis of modeling described above and phantom described above reflectance spectra allow us to make informed selection of optical filters to test in our imaging system. Once the skin phantom described above and inverse optical model selection described above are optimized, the efficacy of system 10 is tested to measure absolute values of melanin and hemoglobin content in the phantoms.

To minimize experimental bias, measurements are performed in a blind fashion. Researchers involved with image acquisition do not have prior information on actual chromophore content and distribution in each phantom. Three sets of images are acquired from each phantom and processed individually to obtain spatial maps of absolute melanin and hemoglobin content. Measured values are compared with actual values to quantify the relative accuracy of the measurements. For phantoms with multiple dermal layers, the accuracy are calculated for each layer.

5 Spectroscopically Validate Chromophore Content Obtained from Images.

We apply a unique spectroscopic technology, SS-FDPM, to make complementary measurements on in-vivo PWS. SS-FDPM is a non-invasive optical technique that utilizes intensity-modulated, near-infrared (NIR) light to quantitatively measure optical properties in tissues. Optical properties derived from SS-FDPM measurements are then used to reconstruct tissue chromophore concentrations. Currently we are able to determine concentrations of oxy-, and deoxy-hemoglobin, water content, and fat content in addition to reduced scattering coefficient. Unlike conventional NIR transillumination methods, SS-FDPM enables quantitative analysis of tissue absorption and scattering parameters in a single non-invasive measurement. Combining both broadband steady-state spectroscopy and frequency-domain photon migration, SS-FDPM allows for the determination of continuous broadband absorption spectra. Successful SS-FDPM measurements have characterized the normal and diseased state of breast tissues in terms of chromophore distribution, as well as monitored the progression of neoadjuvant chemotherapy.

The wavelength range of the SS-FDPM system extends from 400-1000 nm. With this spectroscopic approach, chromophore content deduced from in-vivo skin is compared to those obtained with spectral imaging system 10. Since we do not have prior knowledge of chromophore content distribution in skin, SS-FDPM measurements of chromophore content serve as a validation tool of imaging system 10.

For each patient, band-limited crossed-polarizer digital images are acquired. The number of images will depend on the number of wavelength bands identified as critical for determination of absolute chromophore content as described above. SS-FDPM measurements are acquired from select regions in the imaging field of view. Since SS-FDPM is a contact measurement, we outline the measurement area by tracing a line with a skin marker around the probe. We then acquire a standard, broadband crossed-polarizer digital image to archive the locations of each SS-FDPM measurement for direct comparison with the band-limited crossed-polarizer digital images. Chromophore content values measured with the two instruments are compared and relative accuracy determined. SS-FDPM measured values serve as the "true" values.

The crossed-polarizer digital imaging system 10, as fully developed, provides chromophore concentrations in a reproducible fashion, and that data obtained with system 10 can be used to provide the clinician with objective feedback on PWS treatment with successive patient visits. The invention is thus a reliable quantitative imaging system 10, which is amenable to a variety of clinical applications for which decision making based on clinical "impression" is currently the operating standard. Numerous examples of such applications for which information related to changes in tissue composition is desired include: assessment of treatment of vitiligo and other pigmentary disorders, evaluation of laser induced hyper/hypo pigmentation, and assessment of subsurface changes in vasculature related to skin cancer.

In addition, the use of the invention is not limited to medical or dermatological applications as set forth above in the illustrated embodiments, but can be fully exploited wherever quantitative color measurements of images may be of interest, such as in agriculture or food processing or quality control, textile production or quality control, paint and pigment evaluation, such as in automotive paint or coatings evaluations, and the like. Therefore, it must be clearly understood that the invention is not to be limited by the illustrated examples above, but is more generally defined by the claims set forth below.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

We claim:

1. An apparatus for imaging chromophores in skin comprising:
   a camera;
   crossed-polarizers mounted on the camera through which polarizers an image of the skin is taken; and
   a computer coupled to the camera for taking crossed-polarized image to provide spatially resolved chromophore indices,
   where the camera produces an RGB pixel image and where the computer transforms the image into CIE L*a*b* color space,
   where the computer provides a relative a* image ($\Delta a^*$) of a region of interest modeled pixel-by-pixel on $$\Delta a^* = 100\left(\frac{a^*_{Pws} - a^*_{Ns}}{a^*_{Ns}}\right)$$

where a*PWS is the raw a* indice in the image and a*NS the average a* indices of representative regions of normal skin selected near to the region of interest.

2. The apparatus of claim 1 further comprising a patient positioning device wherein separately taken images of the skin can be registered with each other.

3. The apparatus of claim 1 where the chromophore indices are melanin and erythema indices.

4. The apparatus of claim 1 where the digital camera is a full color camera with adjustable white balance.

5. The apparatus of claim 1 further comprising a macro ring flash illuminator coupled the camera to provide uniform illumination of the skin.

6. The apparatus of claim 1 where the computer provides an image of spatially resolved chromophore indices relating to at least one of the skin conditions comprising port wine stains, vitiligo, pigmentary disorders, psoriasis, or pigmented lesions.

7. The apparatus of claim 1 where the camera is directed to a region of interest on the skin at an optimal view angle to minimize artifacts in color determination resulting from skin curvature dependent on the region of interest.

8. The apparatus of claim 7 further comprising a patient positioning device to stabilize position of the skin relative to the camera including stability of both vertical and horizontal tilt.

9. The apparatus of claim 7 where the computer provides an image at multiple view angles with the optimal view angle to minimize artifacts in color determination resulting from skin curvature determined individually for different regions of interest by the computer.

10. The apparatus of claim 1 where the computer utilizes an experientially determined optimal combination of melanin and erythema metrics to provide relatively independent quantitative measures of melanin and hemoglobin, respectively to analyze images acquired from PWS patients.

11. A method for imaging chromophores in skin comprising:
   taking a crossed-polarized image of the skin; and
   providing an image of spatially resolved chromophore indices based on the crossed-polarized image,
   where providing an image comprises providing an RGB pixel image and transforming the image into CIE L*a*b* color space,
   where providing an image comprises providing a relative a* image (Δa*) of a region of interest modeled pixel-by-pixel on $$\Delta a^* = 100\left(\frac{a^*_{Pws} - a^*_{Ns}}{a^*_{Ns}}\right)$$

where a*PWS is the raw a* indice in the image and a*NS the average a* indices of representative regions of normal skin selected near to the region of interest.

12. The method of claim 11 further comprising stabilizing position of the skin, and taking multiple crossed-polarized images registered with each other.

13. The method of claim 11 where providing an image of spatially resolved chromophore indices based on the crossed-polarized image comprises providing melanin and erythema indices.

14. The method of claim 11 where providing a digital image of skin tissue which is analyzable pixel-by-pixel comprises providing a color image with an adjusted white balance.

15. The method of claim 11 further comprising providing uniform illumination of the skin.

16. The method of claim 11 where providing an image of spatially resolved chromophore indices relating to at least one of the skin conditions comprising port wine stains, vitiligo, pigmentary disorders, psoriasis, or pigmented lesions.

17. The method of claim 11 where taking a crossed-polarized image of the skin comprises minimizing artifacts in color determination resulting from skin curvature dependent on the region of interest by taking an image of a region of interest on the skin at an optimized angle of view.

18. The method of claim 17 further comprising stabilizing the position of the skin relative to both vertical and horizontal tilt.

19. The method of claim 17 where taking a crossed-polarized image of the skin comprises providing an image at multiple view angles with the optimal view angle determined individually for different regions of interest.

20. The method of claim 11 further comprising utilizing an experientially determined optimal combination of melanin and erythema metrics to provide relatively independent quantitative measures of melanin and hemoglobin, respectively to analyze images acquired from PWS patients.

21. An apparatus for quantitative color imaging of an object comprising:
   a color camera;
   crossed-polarizers mounted on the camera through which polarizers an image of the object is taken; and
   a computer coupled to the camera for taking crossed-polarized data to provide an image of spatially resolved color indices
   where the camera produces an RGB pixel image and where the computer transforms the image into CIE L*a*b* color space,
   where the computer provides a relative a* image (Δa*) of a region of interest modeled pixel-by-pixel on $$\Delta a^* = 100\left(\frac{a^*_{Raw} - a^*_{Ns}}{a^*_{Ns}}\right)$$

where a*Raw is the raw a* indice in the image and a*NS the average a* indices of representative regions of normal surface regions selected near to the region of interest.

22. The apparatus of claim 21 where the digital camera is a color camera with adjustable white balance.

23. The apparatus of claim 21 further comprising a macro ring flash illuminator coupled the camera to provide uniform illumination of the object.

24. The apparatus of claim 21 where the computer provides an image of spatially resolved color indices relating to at least one of the surface condition of the object.

25. The apparatus of claim 21 where the camera is directed to a region of interest on the object at an optimized angle of view to minimize artifacts in color determination resulting from surface curvature dependent on the region of interest.

26. The apparatus of claim 25 where the computer provides an image at multiple view angles with the optimal view angle determined individually for different regions of interest by the computer.

27. A method for imaging color content in an object comprising:
   taking a crossed-polarized image of the object; and
   providing an image of spatially resolved chromophore indices based on the crossed-polarized image,
   where providing an image comprises providing an RGB pixel image and transforming the image into CIE L*a*b* color space,
   where providing an image comprises providing a relative a* image (Δa*) of a region of interest modeled pixel-by-pixel on $$\Delta a^* = 100\left(\frac{a^*_{Raw} - a^*_{Ns}}{a^*_{Ns}}\right)$$

where a*Raw is the raw a* indice in the image and a*NS the average a* indices of representative regions of normal surface conditions of the object selected near to the region of interest.

28. The method of claim 27 further comprising stabilizing position of the object, and taking multiple crossed-polarized images registered with each other.

29. The method of claim 27 where providing a digital image of the object which is analyzable pixel-by-pixel comprises providing a color image with an adjusted white balance.

30. The method of claim 27 further comprising providing uniform illumination of the object.

31. The method of claim 27 where providing an image of spatially resolved color indices relating to at least one of the object surface conditions.

32. The method of claim 27 where taking a crossed-polarized image of the object comprises minimizing artifacts in color determination resulting from object curvature dependent on the region of interest by taking an image of a region of interest on the object at an optimized angle of view.

33. The method of claim 32 further comprising stabilizing the position of the object relative to both vertical and horizontal tilt.

34. The method of claim 32 where taking a crossed-polarized image of the object comprises providing an image at multiple view angles with the optimal view angle determined individually for different regions of interest.

* * * * *